(12) United States Patent
Zhao et al.

(10) Patent No.: US 11,688,489 B2
(45) Date of Patent: Jun. 27, 2023

(54) SYSTEMS AND METHODS FOR GROUPING AND COLLAPSING SEQUENCING READS

(71) Applicant: Illumina, Inc., San Diego, CA (US)

(72) Inventors: Chen Zhao, San Diego, CA (US);
Kevin Eric Wu, Oceanside, CA (US);
Sven Bilke, Bethesda, MD (US)

(73) Assignee: Illumina, Inc., San Diego, CA (US)

( * ) Notice: Subject to any disclaimer, the term of this patent is extended or adjusted under 35 U.S.C. 154(b) by 851 days.

(21) Appl. No.: 16/667,642

(22) Filed: Oct. 29, 2019

(65) Prior Publication Data

US 2020/0135298 A1 Apr. 30, 2020

Related U.S. Application Data

(60) Provisional application No. 62/753,786, filed on Oct. 31, 2018.

(51) Int. Cl.
| | | |
|---|---|---|
| G01N 33/48 | (2006.01) | |
| G16B 30/10 | (2019.01) | |
| G06F 16/22 | (2019.01) | |
| G06F 16/2457 | (2019.01) | |
| G16B 30/20 | (2019.01) | |

(52) U.S. Cl.
CPC ......... *G16B 30/10* (2019.02); *G06F 16/2255* (2019.01); *G06F 16/24578* (2019.01); *G16B 30/20* (2019.02)

(58) Field of Classification Search
None
See application file for complete search history.

(56) References Cited

U.S. PATENT DOCUMENTS

2018/0247016 A1* 8/2018 Semenyuk ............. G16B 30/00

FOREIGN PATENT DOCUMENTS

| CN | 106295250 B | 3/2019 |
|---|---|---|
| WO | WO 2016/141294 A1 | 9/2016 |
| WO | WO 2017/004589 A1 | 1/2017 |

OTHER PUBLICATIONS

Buckingham, Lawrence, et al. "Locality-Sensitive Hashing for Protein Classification." AusDM. 2014, pp. 1-7.*
Georganas, E., Buluc, A., Chapman, J., Oliker, L., Rokhsar, D., & Yelick, K. (May 2015), meraligner: A fully parallel sequence aligner. In 2015 IEEE International Parallel and Distributed Processing Symposium (pp. 561-570). IEEE.*
Duan et al., "S-Aligner: Ultrascalable Read Mapping on Sunway Taihu Light" 2017 IEEE International Conference on Cluster Computing. Sep. 5, 2017 (Sep. 5, 2017), pp. 36-46.
"Illumina Dragen Bio-IT Platform v3.2.8 User Guide", Apr. 29, 2019 (Apr. 29, 2019), Retrieved from the Internet: URL:https://support.Illumina.com/content/dam/Illumina-support/documents/documentation/software_documentation/dragen-bio-it/dragen-bio-it-platform-v3.2.8-user-guide-1000000085871-00.pdf [retrieved on Sep. 4, 2020].
International Search Report and Written Opinion issued in application No. PCT/US2020/034395, dated Sep. 14, 2020.
Miller et al., "A 26-hour System of Highly Sensitive Whole Genome Sequencing for Emergency Management of Genetic Diseases" Genome Medicine. 2015, pp. 1-16.
Kendell Clement et al. "AmpUMI: design and analysis of unique molecular identifiers for deep amplicon sequencing", Bioinformatics., vol. 34, No. 13, Jun. 27, 2018 (Jun. 27, 2018), pp. i202-i210.
Konstantin Berlin et al. "Assembling large genomes with single-molecule sequencing and locality-sensitive hashing", Nature Biotechnology, vol. 33, No. 6, May 25, 2015 (May 25, 2015), pp. 623-630.
International Search Report dated Feb. 3, 2020 in corresponding International Application No. PCT/US2019/058476, filed Oct. 29, 2019.

* cited by examiner

*Primary Examiner* — Anna Skibinsky
(74) *Attorney, Agent, or Firm* — Sheppard, Mullin, Richter & Hampton LLP

(57) ABSTRACT

Disclosed herein are systems and methods for collapsing sequencing reads and identifying similar sequencing reads. In one example, a method includes generating a plurality of first identifier subsequences from a first identifier sequence of each nucleotide sequencing read and generating a first signature for the nucleotide sequencing read by applying hashing to the plurality of first identifier subsequences. The method may include assigning the nucleotide sequencing read to a first particular bin of a first data structure based on the first signature and determining a nucleotide sequence for each first particular bin of the first data structure with one or more nucleotide sequencing reads assigned.

29 Claims, 17 Drawing Sheets

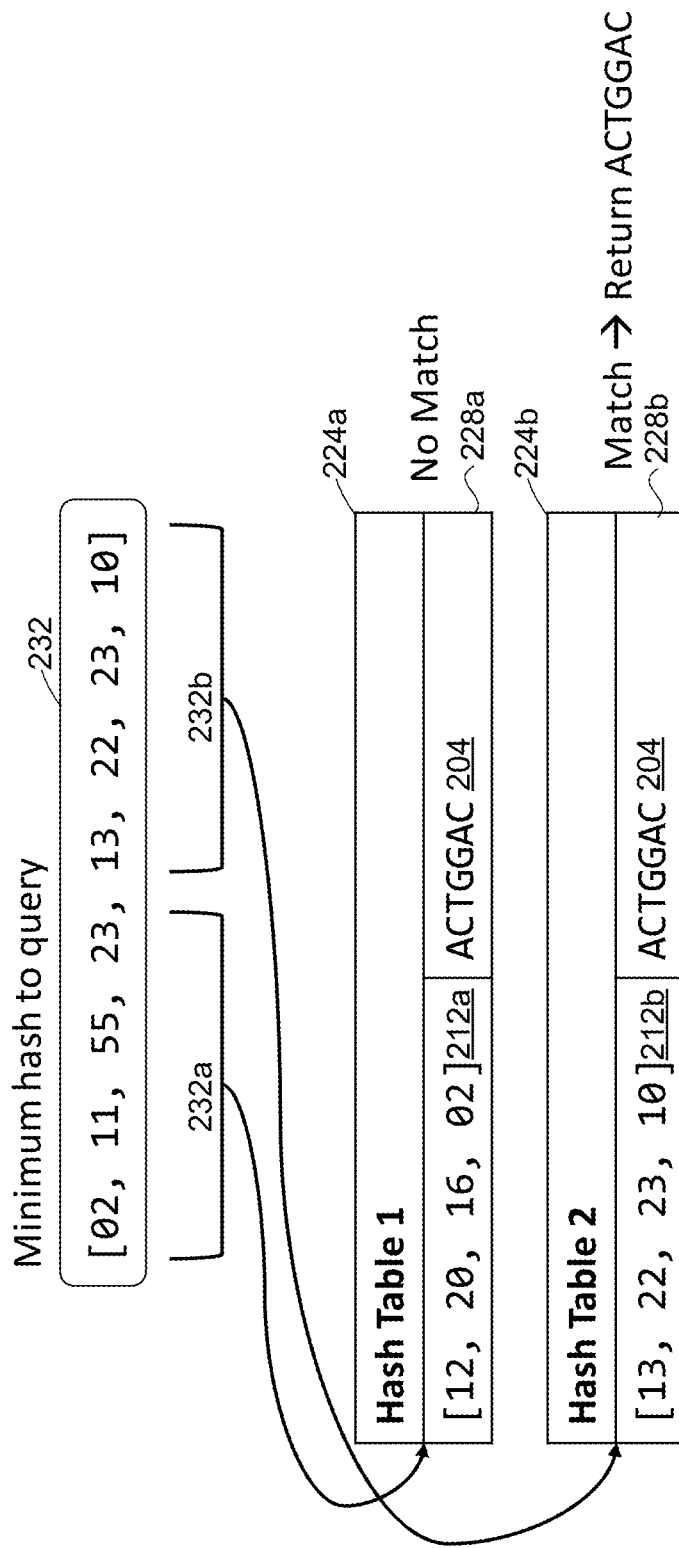

SYSTEMS AND METHODS FOR GROUPING AND COLLAPSING SEQUENCING READS

CROSS-REFERENCE TO RELATED APPLICATIONS

This application claims priority to U.S. Provisional Application No. 62/753,786, filed Oct. 31, 2018, the content of which is incorporate by reference in its entirety.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

Field

The present disclosure relates generally to the field of processing nucleotide sequencing data, and more particularly to collapsing nucleotide sequencing data using locality sensitive hashing.

Description of the Related Art

Read collapsing is a computational method that identifies nucleotide sequencing reads that are output from a sequencing system as originating from the same source deoxyribonucleic acid (DNA) molecule. The sequencing system may be a next generation sequencing (NGS) system, such as the NextSseq instruments from Illumina, Inc. (San Diego, Calif.). Read collapsing may include using statistical methods to reduce spurious errors found in these sets of reads. Read collapsing's resultant in-silico error reduction may be useful for applications within next generation sequencing (NGS), such as detection of variants with ultra-low allele fraction, and in enabling heightened variant calling specificity for clinical applications.

SUMMARY

Disclosed herein are systems and methods for collapsing sequencing reads and identifying similar nucleotides sequences in a plurality of different sequencing reads. In one embodiment, a system includes a non-transitory memory configured to store executable instructions and a first hash data structure for storing nucleotide sequencing reads in a plurality of bins. The system may also include a hardware processor programmed by the executable instructions to perform a method including: receiving a plurality of nucleotide sequencing reads, such as nucleotide sequencing reads 1 of paired-end sequencing reads; for each nucleotide sequencing read: generating a plurality of first identifier subsequences from a first identifier sequence of the nucleotide sequencing read; generating a first signature for the nucleotide sequencing read by applying hashing to the plurality of first identifier subsequences; and assigning the nucleotide sequencing read to at least one first particular bin of the first hash data structure based on the first signature; and determining a nucleotide sequence for each first particular bin of the first hash data structure with one or more nucleotide sequencing reads assigned.

Another embodiment of the invention is a computer-implemented method that includes receiving a plurality of nucleotide sequencing reads, such as nucleotide sequencing reads; for each nucleotide sequencing read: generating a plurality of first identifier subsequences from a first identifier sequence of the nucleotide sequencing read; generating a first signature for the nucleotide sequencing read by applying hashing to the plurality of first identifier subsequences; and assigning the nucleotide sequencing read to a first particular bin of a first data structure based on the first signature; and determining a nucleotide sequence for each first particular bin of the first data structure with one or more nucleotide sequencing reads assigned.

Still another embodiment includes systems and methods for identifying similar nucleotide sequencing reads. In one example, a system includes a non-transitory memory configured to store: executable instructions, a first hash data structure and a second hash data structure for storing a plurality of pairs of sequencing reads; and a hardware processor programmed by the executable instructions to perform a method including: receiving a pair of a first query nucleotide sequencing read and a second query nucleotide sequencing read; generating a plurality of first query identifier subsequences and a plurality of second query identifier subsequences from the first query nucleotide sequencing read and the second query nucleotide sequencing read, respectively. The first and second query nucleotide sequencing read may be the reads of a pair of paired-end sequencing reads. The method may include generating a first query signature and a second query signature for the first nucleotide sequencing read and the second nucleotide sequencing read by applying hashing to the plurality of first query identifier subsequences and the plurality of second query identifier subsequences, respectively; retrieving one or more first stored pairs and one or more second stored pairs from the first hash data structure and the second hash data structure using the first query signature and the second query signature, respectively, wherein each of the first pairs and the second pairs comprises a first stored nucleotide sequencing read and a second stored nucleotide sequencing read; and determining each pair of a first stored nucleotide sequencing read and a second stored nucleotide sequencing read present in both the first stored pairs and second stored pairs as a first sequencing read and a second sequencing read similar to the first query sequencing read and the second query sequencing read, respectively.

Another embodiment is a computer-implemented method that includes receiving a pair of a first query nucleotide sequencing read and a second query nucleotide sequencing read; generating a plurality of first query identifier subsequences and a plurality of second query identifier subsequences from the first query nucleotide sequencing read and the second query nucleotide sequencing read, respectively; generating a first query signature and a second query signature for the first nucleotide sequencing read and the second nucleotide sequencing read by applying hashing to the plurality of first query identifier subsequences and the plurality of second query identifier subsequences, respectively; and retrieving one or more first stored pairs from a first hash data structure, storing a plurality of pairs of sequencing reads, using the first query signature and the second query signature, wherein each of the first pairs comprises a first stored nucleotide sequencing read and a second stored nucleotide sequencing read similar to the first query nucleotide sequencing read and the second query nucleotide sequencing read.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

FIGS. 2A-2D show a schematic illustration of locality sensitive hashing-based read grouping and collapsing, which includes shingling (FIG. 2A), minimum hashing (FIG. 2B), locality sensitive hashing (LSH) insertion (FIG. 2C), and LSH querying (FIG. 2D). Given a query sequencing read (not shown), a minimum hash or a signature 232 of the query sequencing read may be generated, and the minimum hash 232 may be partitioned into two chucks 232a, 232b that are used to query against hash tables 1 and 2 (224a, 224b). The query sequencing read is similar, but not identical, to the sequence ACTGGAC 204 stored in the hash tables 1 and 2 (224a, 224b). The minimum hash 232 of the query sequencing read is generated similar to how the minimum hash 212 is generated for the sequencing read ACTGGAC (204) illustrated in FIGS. 2A and 2B. Since the hash table 1 (224a) does not include one of the chucks 232a as a key 212a of an existing bin 228a, no sequencing read similar to the query sequencing read is found in the hash table 1 (224a). Since the hash table 2 (224b) includes one of the chucks 232b as a key 212b of an existing bin 228b, the query sequencing read is similar to the sequencing read 204 associated with the existing bin 228b. The sequence ACTGGAC (204) stored in the existing bin 228b is then returned as a sequencing read that is similar to the query sequencing read.

DETAILED DESCRIPTION

Figure 1:
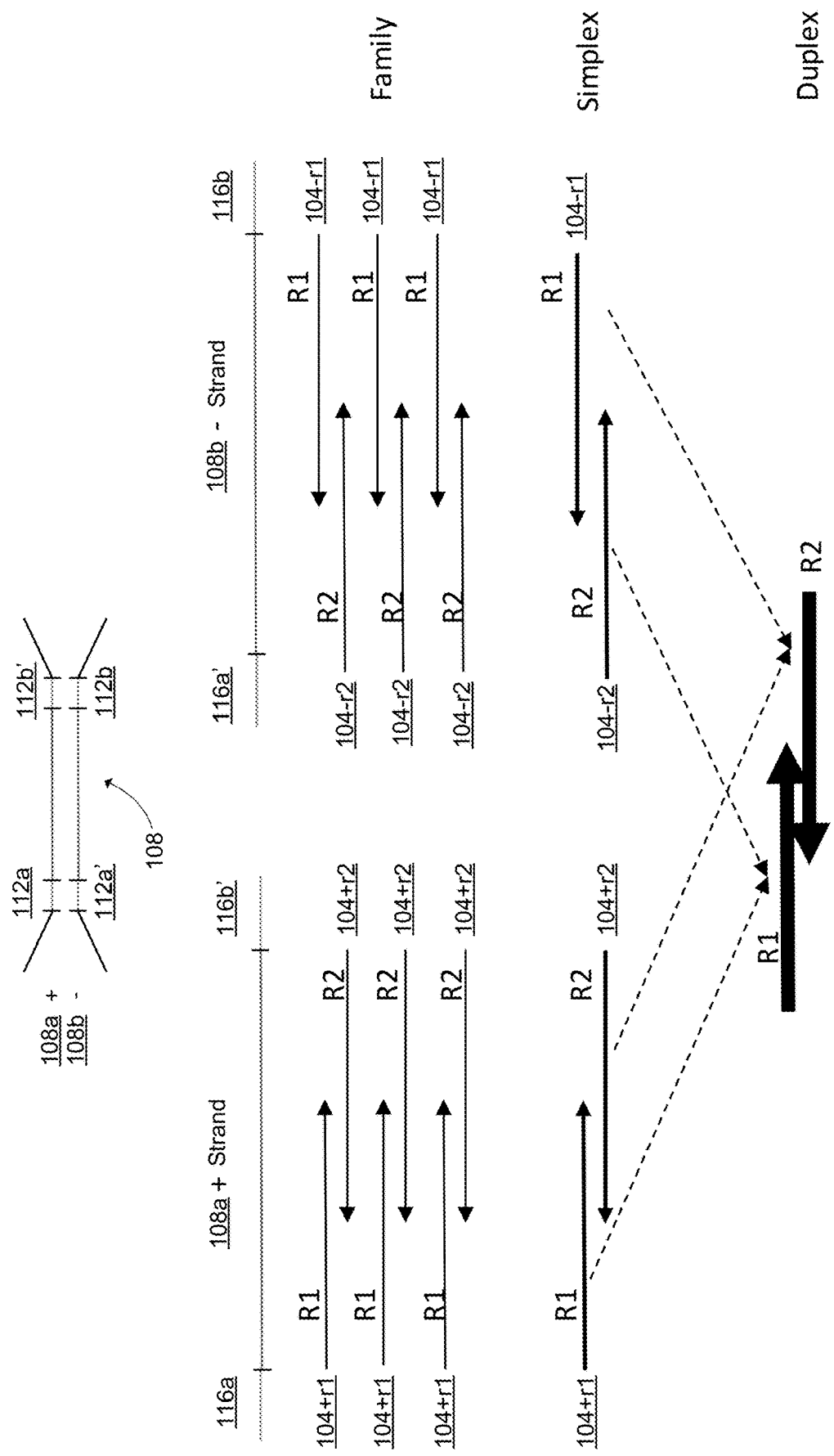
FIG. 1 shows a schematic illustration of collapsing sequencing reads.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

Overview

Read collapsing is a computational method that identifies nucleotide sequencing reads as originating from the same source deoxyribonucleic acid (DNA) molecule, and subsequently uses statistical methods to reduce spurious errors found in these sets of reads. Referring to FIG. 1, given all the duplicate reads 104+r1, 104+r2, 104−r1, 104−r2, of the same DNA molecule 108 with a plus strand 108a and a minus strand 108b, read collapsing may include grouping those reads 104+r1, 104+r2, 104−r1, 104−r2 together. Read collapsing may include using statistical voting to reduce spurious errors, such as with simplex collapsing to determine the nucleotide sequence of a nucleotide strand, such as the sequence of the plus strand 108a of a DNA molecule 108. Read collapsing may include inferring the sequence of the original DNA molecule 108 with high confidence, such as with duplex collapsing to determine the nucleotide sequence of a DNA molecule 108 from both the sequence of the plus strand 108a and the sequence of the minus strand 108b. The systems and methods disclosed herein may utilize locality sensitive hashing (LSH) and virtual identifier sequences (vID sequences) for read collapsing.

Read collapsing may produce high-quality reads. Read collapsing may require that a sample be sequenced with identifier sequences (ID sequences) 112a, 112b', 112a', 112b. Such identifier sequences are also referred to herein as "physical identifier sequences" (pID sequences). These identifier sequences may be universal molecular indices (UMI) barcodes. Such identifier sequences 112a, 112b', 112a', 112b enable increased resolution when distinguishing reads and molecules that may appear very similar otherwise, though read collapsing may be performed without such identifier sequences under specific circumstances. Read collapsing may result in in-silica error reduction. Such error reduction may be useful for many applications within next generation sequencing (NGS).

One application of this process is detection of variants that are only present in ultra-low allele fractions, such as in circulating tumor DNA (ctDNA). Another application is heightened variant calling specificity for clinical applications. Since read collapsing effectively combines all the duplicate observations of a DNA fragment, such as PCR duplicates of a DNA fragment, into a single representative, read collapsing has the benefit of significantly reducing the amount of data that needs to be processed downstream. Removing duplicate observations, or reads, may result in a ten fold, or more, decrease in data size.

A naïve read collapsing method may involve exhaustive pairwise sequence comparisons, which requires a runtime of $O(n^2)$. $O(n^2)$ is insurmountable for NGS data. For example, around 600 million read pairs ($6*10^8$) may be produced from a sample. Exhaustive pairwise sequence comparisons may require $3.6*10^{17}$ comparisons. Even at the speed of one comparison per nanosecond, $3.6*10^8$ seconds, which equals approximately 4,167 days, would be required to compute the pairwise comparisons. Even with 56 processing cores, it may still take over two months of compute time to analyze a single sample.

Conventional read collapsing methods may use a combination of alignment position and UMI barcode information to identify groups of duplicate reads. One downside of these methods of read collapsing is that such methods require input reads that have already been aligned and sorted. There are challenges associated with the preprocessing of the reads being aligned and sorted prior to read collapsing. First, conventional read processing requires $O(n*log(n))$ preprocessing. Aligning "n" reads may requires a runtime of $O(n)$. Sorting "n" reads requires a run time of $O(n*log(n))$. The preprocessing of aligning and sorting "n" reads requires a runtime of $O(n*log(n))$.

The overall process of collapsing reads using a conventional method has a lower-bound runtime of $O(n*log(n))$. This super-linear function means that runtime grows faster than the input size. As more raw sequencing data is generated, the computational cost associated with conventional read collapsing grows more quickly than the amount of sequencing data being processed. In addition, conventional read collapsing is constrained to well-characterized references. Basing read collapsing upon nucleotide alignments constrains its usage to applications where high-quality reference sequences exist, as these reference sequences are necessary to enable good alignments, and subsequently accurate collapsing. For example, reasonably good alignments may not be available for structural variants, repeat expansions, and repetitive genomic regions. Dependency on alignment makes using read collapsing technologies (and UMI technologies) on novel or unknown species difficult, limiting the generality of UMI-enabled error reduction technologies. Read collapsing could have great impacts in these arenas, as there is no high quality "reference" to help identify sequencing errors.

Disclosed herein are systems and methods for read collapsing using locality sensitive hashing (LSH). Conventional read collapsing approaches have required alignment information, because there was no good alternative method for sub-grouping reads that already shared a UMI barcode. A LSH-based read collapsing method as disclosed herein addresses this shortcoming, and removes the dependency of collapsing on having an alignment, enabling huge gains in algorithmic complexity, and in general applicability of read collapsing and related technologies.

In one embodiment, the LSH-based read collapsing method does not have a runtime of $O(n*log(n))$ and does not require a well-characterized reference. For example, the read collapsing method may not require alignment information at all, much less sorted alignments. In one implementation, the method relies on physical identifier sequences (pID sequences), such as physical UMI barcodes (pUMI barcodes), and virtual identifier sequences (vID sequences), such as virtual UMI barcodes (vUMI barcodes) to identify groups of duplicated reads present on the various nucleotide fragments. Physical identifier sequences also referred to herein as "identifier sequences" (ID sequences). Physical UMI barcodes are also referred to herein as "UMI barcodes." A virtual identifier sequence may be a subsequence of a read acting as a "virtual" identifier sequence to identify groups of duplicated reads. A vUMI barcode may be a subsequence of a read acting as a "virtual" barcode to identify groups of duplicated reads. A physical identifier sequence or a physical UMI barcode may be an identifier sequence or barcode added to nucleotide fragments during sequencing library preparation.

In one embodiment, the method groups together similar reads and does not require any reference sequence, or exhaustive sequence comparisons. The method may include determining a first-pass naïve grouping of reads into bins defined by UMI barcodes, such as physical UMIs, virtual UMIs, or a combination thereof. The method combines virtual UMIs with locality sensitive hashing. Since the method allows reads with similar sequences to be grouped together without their alignment information, the method decouples the process of read collapsing from the constraints of alignment. The method can include determining similar sequences comprising checking other sequencing reads in that bin.

The method may be used to collapse reads from any sample, such as DNA or RNA, regardless of the organism the sample is derived from. Furthermore, since hashing is a $O(1)$ constant time operation, and hashing needs to performed a fixed number of times for each of n reads, the method enables read collapsing that runs in $O(n)$ runtime. For example, hashing has to be performed once, twice, thrice, or more, for each of n reads. Such read collapsing runtime reduces the required processing time for the increasingly large sets of data generated with NGS. The $O(n)$ runtime enables significant reduction in runtime complexity of secondary analysis and allows flexible application of read collapsing to any sample.

In one embodiment, a DNA sequencing instrument may implement the LSH-based read collapsing method disclosed herein. For example, the method may be implemented as an on-instrument method for in-silica error reduction since the method does not require a reference sequence for read collapsing. The method may achieve greatly reduced error rates for all sequencing reads by leveraging duplication rates of NGS to perform error reduction. The method may also significantly reduce the amount of sequencing data that users would have to process, thus increasing the accessibility of genomic analyses. The method may be utilized as an on-sequencer technology to output fewer, higher-quality reads for customers, reducing complexity of downstream analyses.

In one embodiment, the sequencing reads are not associated with, or generated using, UMI barcodes. For example, locality sensitive hashing may be performed on virtual UMIs to group the nucleotide reads. As another example, "tiered" virtual UMI strategies may be used to mimic the binning functionality provided by physical UMI barcodes. The method may generate two types of virtual UMIs, one used as mimics of physical UMIs, and one used as virtual UMIs.

Duplicate marking is a bioinformatics method for reducing bias introduced by PCR. Disclosed herein includes systems and methods for grouping together similar read sequences and marking duplicates with locality sensitive hashing.

Read Collapsing

Disclosed herein includes systems and methods for read collapsing. In one embodiment, the method uses virtual identifier (vID) sequences, such as virtual universal molecular indices (vUMIs), with locality sensitive hashing to enable reference-free grouping of similar reads without performing exhaustive pairwise comparisons. A virtual identifier sequence, such as a virtual UMI, of a sequencing read refers to any substring or subsequence within the sequencing read itself, including potentially noncontiguous substrings. A virtual identifier sequence is different from a physical identifier (pID) sequence. A physical identifier sequence, such as a physical UMI (pUMI), refers to an identifier sequence or UMI barcode added during sequencing library reparation.

Locality sensitive hashing (LSH) is a computational method that places "similar" data into the same computational "bins" without performing exhaustive pairwise comparisons. Data similarity refers to sequence similarity of reads, which may be computed with metrics such as Levenshtein distance, Hamming distance, or Jaccard distance. The LSH function may "hash" the virtual UMI associated with each read, and use the result to place each read in a bin, alongside reads with similar virtual UMIs. LSH as applied to sequencing reads as disclosed herein enables sequencing reads with virtual UMIs that contain errors to be grouped together based on the virtual UMIs. Sequencing technologies oftentimes do not generate error free sequencing reads. Thus, being able to bin together and quickly find similar sequences which may carry small mutations is important to performing the read grouping necessary to perform read collapsing. Because the small mutations in sequencing reads are often difficult to predict, general methods for grouping similar sequencing reads may be more useful than specific methods for grouping similar sequencing reads that assume specific mutation patterns. In some implementations, the error tolerant properties of the method disclosed herein come into play in approximately 20% of sequencing reads. If left uncorrected, these sequencing reads may greatly impact collapsing accuracy and subsequently manifest themselves as a plethora of false positives in variant calling.

In one embodiment, similar sequencing reads may be identified based on virtual UMIs generated from the sequencing reads by sorting virtual UMIs, for example, lexicographically. A read collapsing method based on sorting virtual UMIs may not account for mutations in the virtual UMIs, and may have a runtime complexity of $O(n*\log(n))$. In another embodiment, similar sequencing reads may be identified using naïve, canonical hashing with virtual UMIs. A read collapsing method based on naïve, canonical hashing may have similarly performance compared to the LSH-based read collapsing method. Such read collapsing method does not have error-tolerant properties. In one embodiment, similar sequencing reads can be identified by clustering UMIs associated with sequencing reads. A clustering-based read collapsing method can handle slightly mismatched virtual UMI barcodes, but would involve $O(n^2)$ pairwise comparisons, which is significantly worse than $O(n*\log(n))$ for runtime of a conventional read collapsing method and $O(n)$ runtime of LSH-based read collapsing method.

LSH is a probabilistic data process. The probability of placing similar read data in the same bin with LSH is high. There exists a small, nonzero probability that similar data does not fall in the same bin. There may be a small chance that similar data does not fall in the same bin, or different data falls in the same bin. In one embodiment, a LSH is designed in order to minimize the probability of placing similar read data in the same bin with LSH. In one embodiment, the LSH-based read collapsing method can be configured to for maximum recall and perform an alignment-based check for each item in each bin (usually fewer than 5 items).

Locality Sensitive Hashing Applied to Sequences

Locality sensitive hashing (LSH) passes each piece of data, such as a virtual UMI of the data, through a "hash" function whose result is used to place that data into a bin. With LSH, similar data should fall in the same (or nearby) bins, enabling very fast queries for similar data. LSH-based read collapsing may include shingling, min hashing, and locality sensitive hashing. Shingling includes digesting input data into overlapping sets or shingles of characters of length k. Min hashing includes passing each "shingle" through a set of hash functions to generate a fingerprint or signature for the data. Locality sensitive hashing includes using the fingerprint to place data into "bins" where similar data is likely to share a similar binning scheme. For example, a sequencing read can be digested into subsequences of length k of the sequencing read. Each subsequence can be passed through a set of hash functions to generate a signature of the sequencing read. The signature can be used to place the sequencing read into one or more bins where similar sequencing reads are likely to share a similar or identical signature.

Figure 2A:
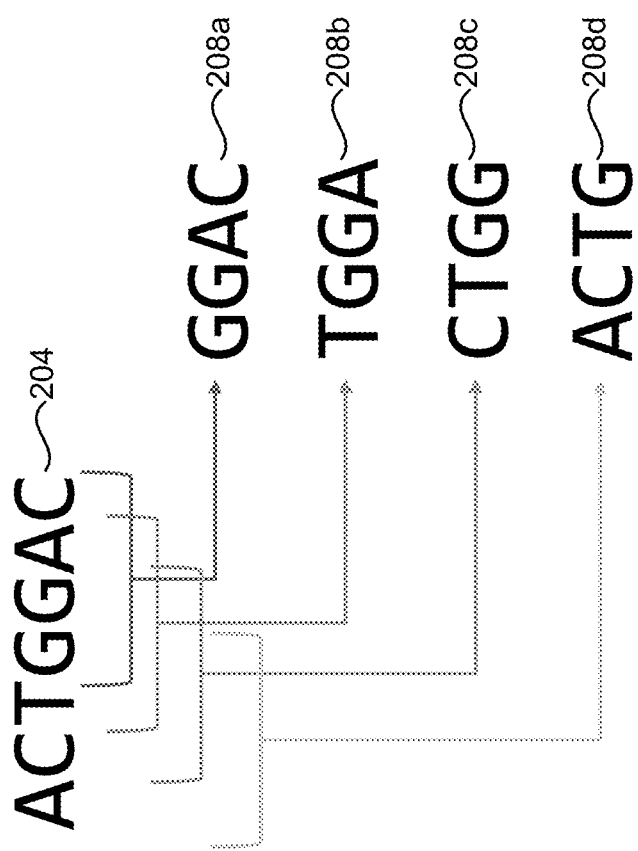

FIGS. 2A-2D show a schematic illustration of locality sensitive hashing-based read grouping and collapsing, which includes shingling (FIG. 2A), minimum hashing (FIG. 2B), locality sensitive hashing (LSH) insertion (FIG. 2C), and LSH querying (FIG. 2D). Shingling includes moving a sliding window of k bases by m-base pair increments, thus digesting a virtual UMI 204 into k-mer "shingles" 208a-208d (FIG. 2A). For example, a sliding window of 4 bases can be moved by 1-base pair increments to digest a virtual UMI 204 into 4-mer singles. FIG. 2A shows four shingles of sequences. The first shingle is GGAC (208a), the second shingle is TGGA (208b), the third shingle is CTGG (208c), and the fourth shingle is ACTG (208d).

Figure 2B:
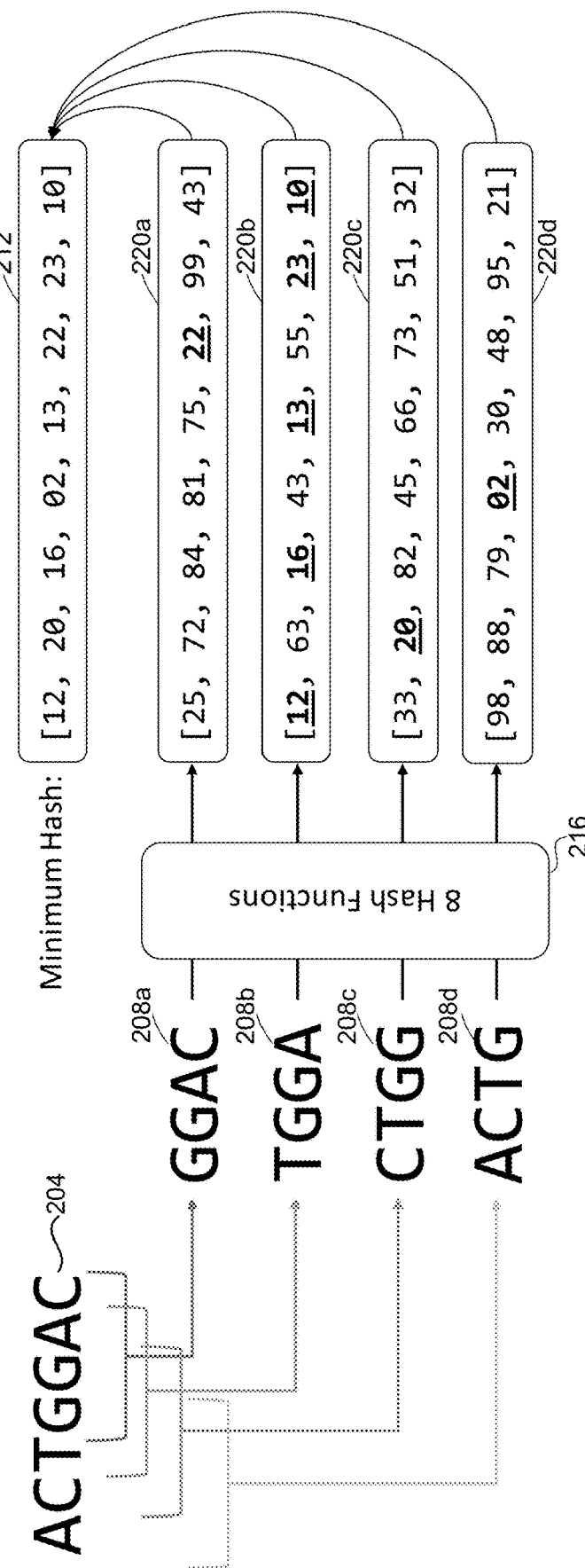

Min hashing includes generating a hash "signature" 212 for the k-mer set of shingles by passing the set through several hash functions 216, and taking the minimum hash (MinHash). FIG. 2B illustrates that the set of four shingles GGAC, TGGA, CTGG, and ACTG may be passed to eight hash functions 216 to generate, for each shingle, an output 220a-220d, respectively, of eight elements of the eight hash functions. The number of hash functions can be 8, 16, 32, 64, 128, 256, 512, 1024, or more. The minimums of the corresponding elements of the hash outputs 220a-220d may be taken to compute a minimum hash 212 of the minimums. The Jaccard distance of the minimum hash is an approximation of true Jaccard distance. The more hash functions, the better the approximation is.

Figure 2C:
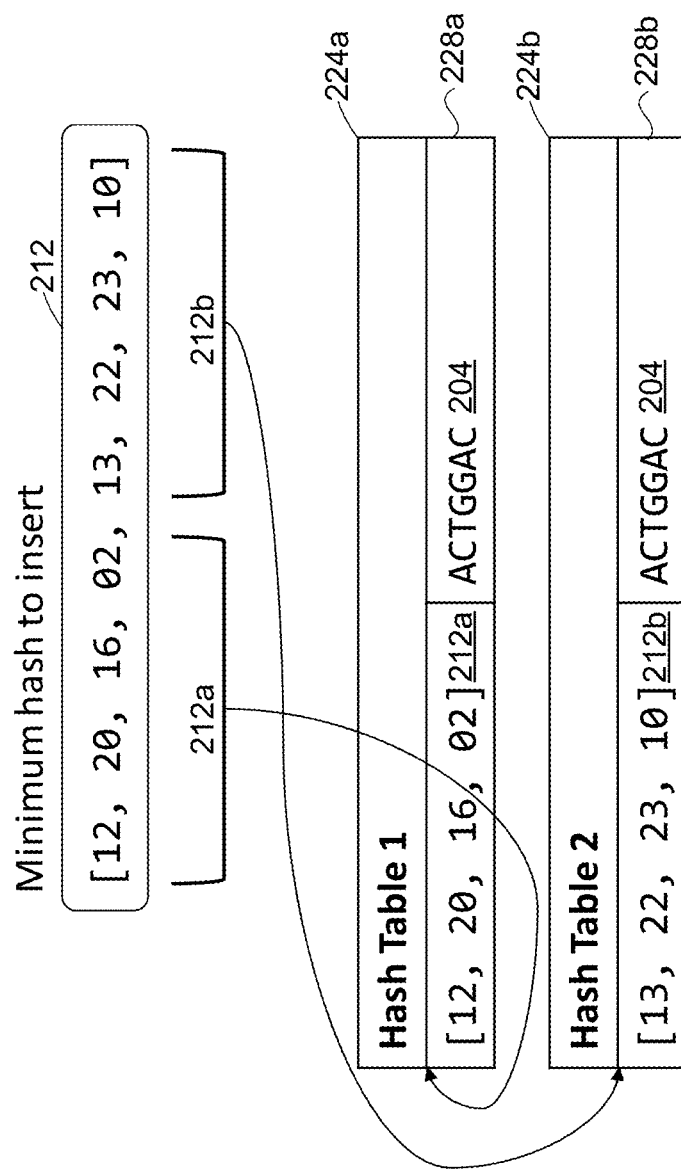

Referring now to FIG. 2C, the sequencing read 204 may be inserted into hash tables 224a, 224b based on the minimum hash 212, or subsequences 212a, 212b of the minimum hash 212, computed from the sequencing read 204. FIG. 2C illustrates that a sequencing read 204 may be inserted into hash tables 224a, 224b based on subsequences 212a, 212b of the minimum hash 212. LSH insertion of a sequencing read 204 consumes a hash "signature" 212 and then partitions the signature 212 into chunks or subsequences 212a, 212b. Those chunks 212a, 212b are then used as keys in hash tables 224a, 224b, in particular in bins 228a, 228b of the hash tables 224a, 224b. This partitioning and hashing scheme is tunable for "wideness" of bins and for higher recall or higher specificity. As shown in FIG. 2C, the same sequencing read 204 is placed in two different bins in two different hash tables 224a, 224b. As long as two sequencing reads share, or are stored in, one or more bins, the sequencing reads may be considered similar.

FIG. 2D illustrates determining whether a query sequencing read is similar, or identical, to a sequencing read stored in a hash table using LSH. Given a query sequencing read, the system passes the query sequencing read through minimum hashing, and queries the minimum hash against all hash tables. A signature 232 of the query sequence can be partitioned to two chunks 232a, 232b, which are queried against all hash tables 224a, 224b. Since the hash table 2 (224b) includes one of the chucks 232b as a key 212b of an existing bin 228b, the query sequence is similar, or identical, to the sequencing read 204 associated with, such as stored in, the existing bin 228b.

Locality Sensitive Hashing Applied to Sequences

Figure 3:
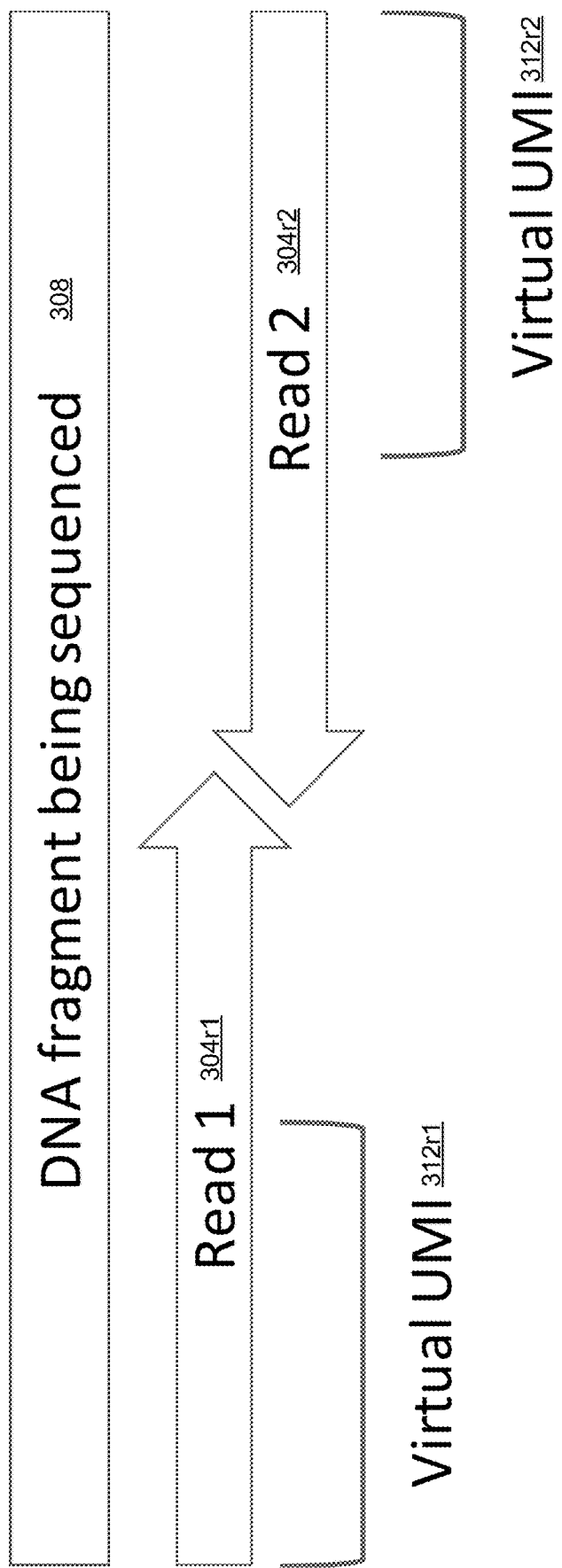
FIG. 3 shows a schematic illustration of generating virtual universal molecular indices (vUMIs) for a Read 1 and a Read 2 of paired-end sequencing reads.

A virtual UMI is a subsequence of a sequencing read itself. A virtual UMI may span up to the entire nucleotide read, and may be a contiguous subsequence or a noncontiguous subsequence. For example, a virtual UMI of a sequencing read can be 25 base pairs (bps) from the 5' end of the sequencing read. FIG. 3 shows a schematic illustration of generating virtual universal molecular indices (vUMIs) for a Read 1 (R1) and a Read 2 (R2) of paired-end sequencing reads. A Read 1 304r1 and a Read 2 304r2 of paired-end sequencing reads corresponding to a positive strand, or a negative strand, of a DNA fragment 308 being sequenced may be processed to generate virtual UMIs 312r1, 312r2.

Figure 4A:
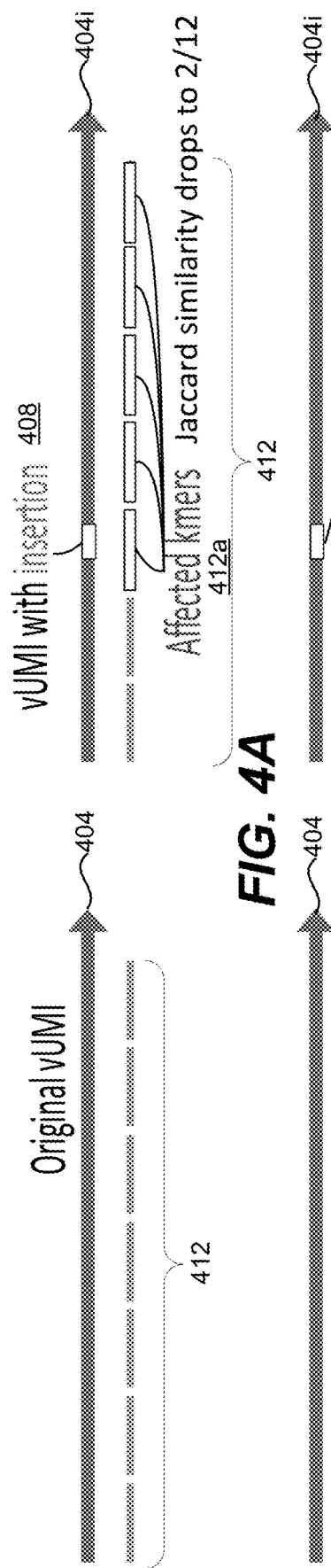
FIGS. 4A and 4B show schematic illustrations of generating k-mers (FIG. 4A) and tiled k-mers (FIG. 4B) from virtual UMIs.
Figure 4B:
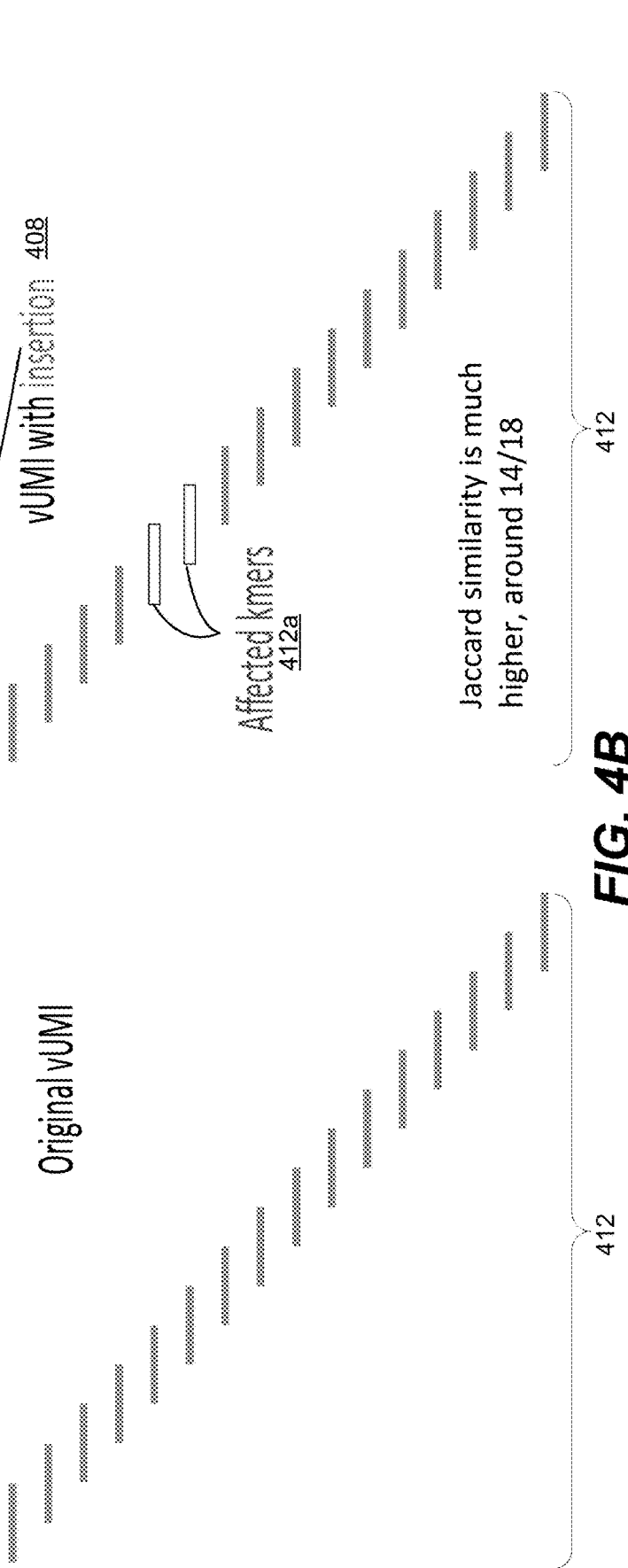

FIGS. 4A and 4B show schematic illustrations of generating k-mers (FIG. 4A) and tiled k-mers (FIG. 4B) from virtual UMIs. The Jaccard similarity of two sets of k-mers is the number of k-mers that both sets contain. The Jaccard similarity of two identical virtual UMIs can be 7/7 if 7 k-mers 412 are generated for the virtual UMIs. As illustrated in FIG. 4A, the Jaccard similarity of a virtual UMI 404 and the same virtual UMI 404i except for an insertion 408 can be 2/12, because all k-mers 412a that include the insertion 408 or 3' of the insertion are affected. Usage of overlapping k-mers across virtual UMI allows better tolerance of insertions and deletions. As illustrated in FIG. 4B, with the same insertion illustrated in FIG. 4A, the Jaccard similarity of the virtual UMI 404 and the same virtual UMI 404i except for an insertion 408 is still high at 14/18 if 16 k-mers 412 are generated for the virtual UMIs 404, 404i. The Jaccard similarity is still quite high because only k-mers 412a that include the insertion 408 are affected by the insertion 408. Greater similarity after shingling leads to more similar MinHash signatures, which in turn helps altered sequences land in the same LSH bin.

In one embodiment, LSH itself does not directly store or index the groups of reads that are to be collapsed. Rather, LSH aids in finding similar reads to a given query read. Once a similar read is found, it is stored in a conventional hash table where the key is the "centroid" read that first started that group. In other words, the LSH data structure contains the same "keys" as the aforementioned conventional hash table (and the two are updated in lockstep), where these "keys" are reads that serve as "group anchors" to which other reads are assigned if they are similar. LSH enables an incoming read to quickly find the keys/anchors that it might match against, such that exhaustive checks or comparisons are not required. The actual groups or sequencing reads may be stored in conventional hash tables.

Alignment Score Check.

An alignment score check may be performed after checking the LSH bin for similar sequences. The alignment score check ensures that dissimilar virtual UMIs are not equated or considered similar. A minimum alignment score for virtual UMIs may be required for the virtual UMIs to be considered equivalent. When performing the alignment check against LSH matches, the best match may be used to determine the alignment score is above a threshold (i.e., with the highest alignment score). More mismatches, such as single nucleotide variants (SNVs) and insertions and deletions (indels) reduces alignment score. "Sliding" an alignment reduces the number of matches, which then, in turn reduces the number of mismatches tolerated. In one embodiment, global alignment of virtual UMIs may be performed, which can be computationally expensive.

Dual-Bin LSH Structure for vUMI Matching

The two virtual UMIs from each read pair are "independent" barcodes, or independent measures of identity of the same DNA fragment. By maintaining two separate LSH data structures for each virtual UMI, false positives may be reduced. Because fewer MinHash signatures are placed into each bin, there is a lower chance of an unintended collision. By intersecting the result of two independent queries, most remaining false positive hits can be removed without losing the correct hits.

Independent LSH data structures may be used for the virtual UMI on read1 and on read2. LSH may be configured for very high recall with suboptimal specificity. To improve specificity, the intersection between two orthogonal queries can be taken to improve specificity without much impact to sensitivity. Separating virtual UMIs from read 1 and read 2 improves specificity in more repetitive regions as well.

In one embodiment, there can be 64 hashes for each k-mer. A Read 1 has a minHash signature of 64 elements and a Read 2 has a minHash signature of 64 elements. The pair of Read 1 and Read 2 may be stored in two hash tables of a dual-bin LSH structure based on the minHash signature of the Read 1 and the minHash signature of the Read 2, respectively. The minHash signature of Read 1 can be divided into subsequences so that the pair of Read 1 and Read 2 can be stored in multiple bins of one hash table and in multiple bins of the other hash table. The number has hashes can be different in different implementations, such as 8, 64, 256, 1024, and more. More hashes can be used for more accurate data structure performance at the expense of slightly slower runtime, and fewer hashes can be used for slightly less accurate data structure performance with the addition of faster runtime. Every k-mer is hashed the same number of times, whether that is 64 times, 8 times, or n times, to ensure that the minhash signatures are of consistent size.

In one embodiment, a read 1 and a read 2 are considered an atomic, inseparable unit, and that this atomic unit is referred to by both the MinHash signature of the virtual UMI from read 1, and by the MinHash signature of the virtual UMI from read 2 (vUMI 1 and vUMI 2). Within each hash table, the MinHash signature can be divided into parts such that the atomic read 1/read 2 pair is stored in multiple bins, once for each chuck of the signature.

Exemplary pseudocode of a dual-bin LSH structure is shown below.

```
Class DualBinLSH( ):
    self.matcher1 = LSH( )
    self.matcher2 = LSH( )
    func get_match(vUMI1, vUMI2):
        x = self.matcher1.query(vUMI1)
        y = self.matcher2.query(vUMI2)
        # Filter out spurious matches via vUMI alignment
        z = [items in intersect(x, y) with aln score ≥ cutoff]
        return argmax(z) # return match with best aln score
    func has_match(vUMI1, vUMI2):
        if self.get_match(vUMI1, vUMI2) is not null/empty:
            return True
        return False
    func insert(vUMI1, vUMI2):
        self.matcher1.insert(vUMI1)
        self.matcher2.insert(vUMI2)
```

Exemplary pseudocode of using a dual-bin LSH structure in LSH is shown below. By inserting a pair of virtual UMIs with no similar virtual UMIs stored in the dual-bin LSH structure allows future queries to find the inserted pair. In essence, a new "seed" is created for a family that may be matched against next time.

```
func bin_reads_by_virtual_UMI(reads w/ same UMIs):
    Matcher = DualBinLSH( )
    Families = HashTable( )
    for read_pair in reads:
        vUMI_1, vUMI_2 = read_pair.get_virtual_umis( )
        if Matcher.has_match(vUMI_1, vUMI_2):
            match = Matcher.get_match(vUMI_1, vUMI_2)
            Families[match].extend(read_pair)
        else:
            Families[(vUMI_1, vUMI_2)] = List(read_pair)
            Matcher.insert(vUMI_1, vUMI_2)
    return Families
```

Dual-Bin LSH Structure for vUMI Matching

Figure 5:
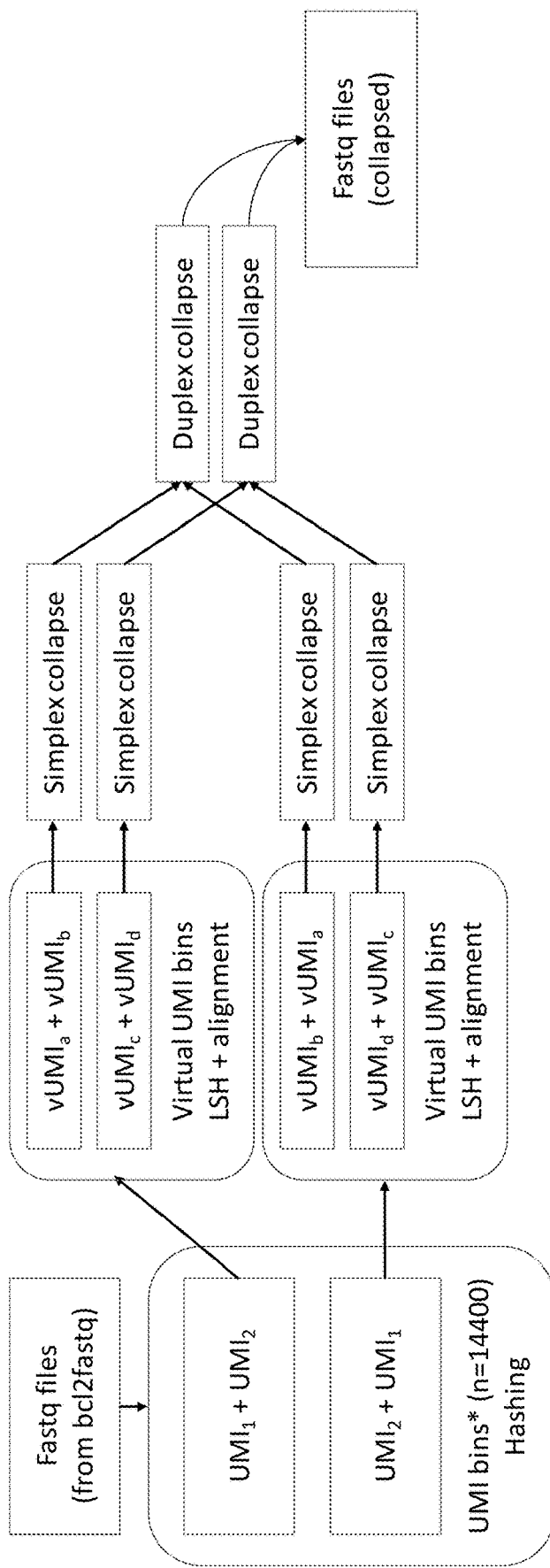
FIG. 5 shows a flow diagram of binning sequencing reads via their sequences and their hashes. Each physical UMI barcode may be selected from one of 120 possible physical UMI barcodes such that there are 120×120=14,400 combinations of physical UMI barcodes for each pair of sequencing read 1 and read 2. In the flow diagram, each pair of sequencing read 1 and read 2 can be assigned to one of 14,400 UMI bins based on the combination of physical UMI barcodes of the pair. The read collapsing method of the disclosure may be applied to the sequencing reads of each UMI bin.

FIG. 5 shows a flow diagram of binning sequencing reads via their sequences and their hashes. The binning process illustrated in FIG. 5 is parallelizable, which may result in linear speedup with thousands of threads. The binning process illustrated requires intermediate caching with minimal memory usage. Each physical UMI barcode may be selected from one of 120 possible physical UMI barcodes such that there are 120×120=14,400 combinations of physical UMI barcodes and each pair of sequencing read 1 and read 2 can have one of the 14,400 combinations of physical UMI barcodes. LSH can be applied to the sequencing reads associated with each pair of physical UMIs in parallel.

Simplex collapsing refers to collapsing all sequences that share the same physical+virtual UMI pairings in the same order. Because these sequences have their barcodes in the same order, this indicates that these sequences were derived not only from the same DNA molecule, but also from the same strand of that DNA molecule. In simplex collapsing, every read in a group/family has the same first UMI, the same second UMI, the same first virtual UMI, and the same second virtual UMI. Multiple reads can satisfy this condition, in which case they are all considered to be reads coming from the same strand of the same molecule.

After simplex collapsing is performed, duplex collapsing may be performed. In duplex collapsing, given a collapsed read pair, an attempt is made to find another simplex molecule that has the same physical and virtual UMI pairings in reverse order—this is analogous to finding the opposite strand of that same DNA molecule. If such a duplex match is found, then duplex collapsing is performed.

Because duplex collapsing is performed subsequent to simplex collapsing, all the strand-specific duplicates have been removed with simplex collapsing. In duplex collapsing, the already-collapsed reads from the opposite strand from the same molecule are found. For example, given a collapsed read pair with first UMI x, second UMI y, first virtual UMI a, and second virtual UMI b, duplex collapsing looks for the opposite strand's read pair which will have its first UMI be y, its second UMI be x, its first virtual UMI be b, and its second virtual UMI be a. No reverse complementing of the opposite strand's read pair may be required due to the semantics of how reads are reported in the output files, such as "fastq" files. This two-tiered single-strand then cross-strand collapsing enables some advanced variant calling techniques in downstream analyses.

Results

Read collapsing results between conventional alignment-based methods and the LSH/virtual UMI-based methods were found to be comparable, both on the level of alignment summary metrics, and when it came to variant calling, such as structural variant calling and small variant calling. To find similar nucleotide sequences, other items in the bin can be checked. The virtual UMI-based methods disclosed herein may thus be used for collapsing sequencing reads for variant calling.

Figure 6A:
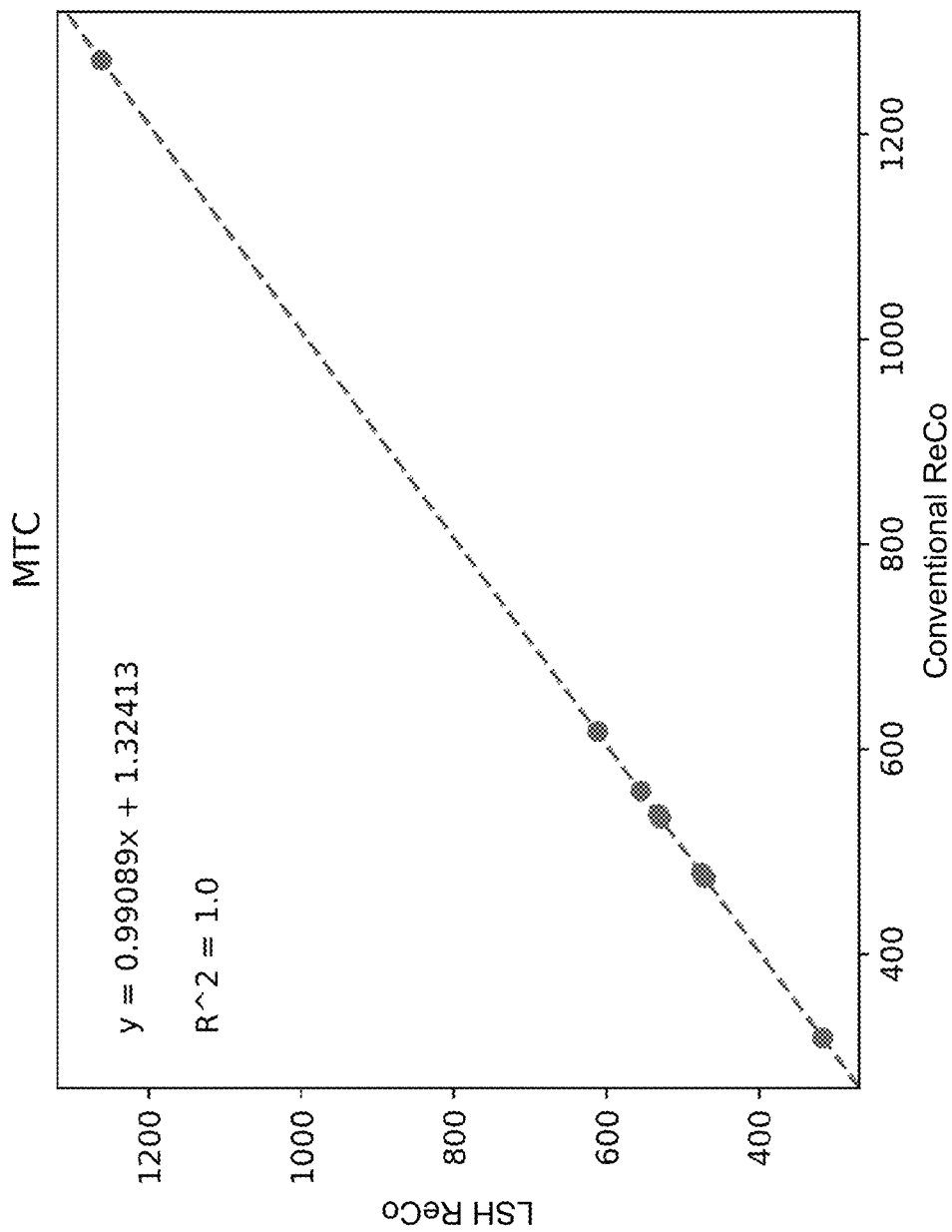
FIGS. 6A-6F are exemplary plots showing that read collapsing with locality sensitive hashing and alignment-based read collapsing have similar performance.
Figure 6B:
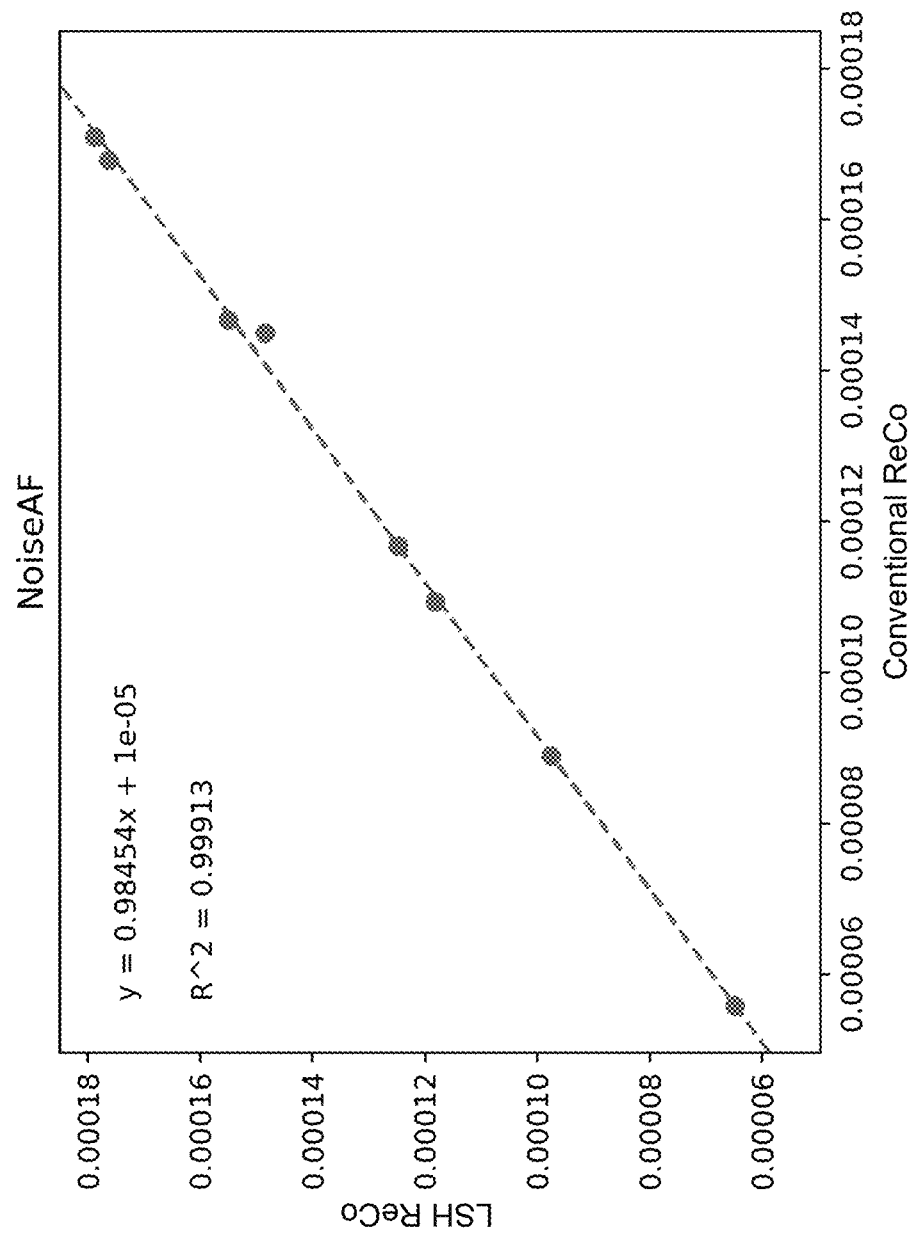
Figure 6C:
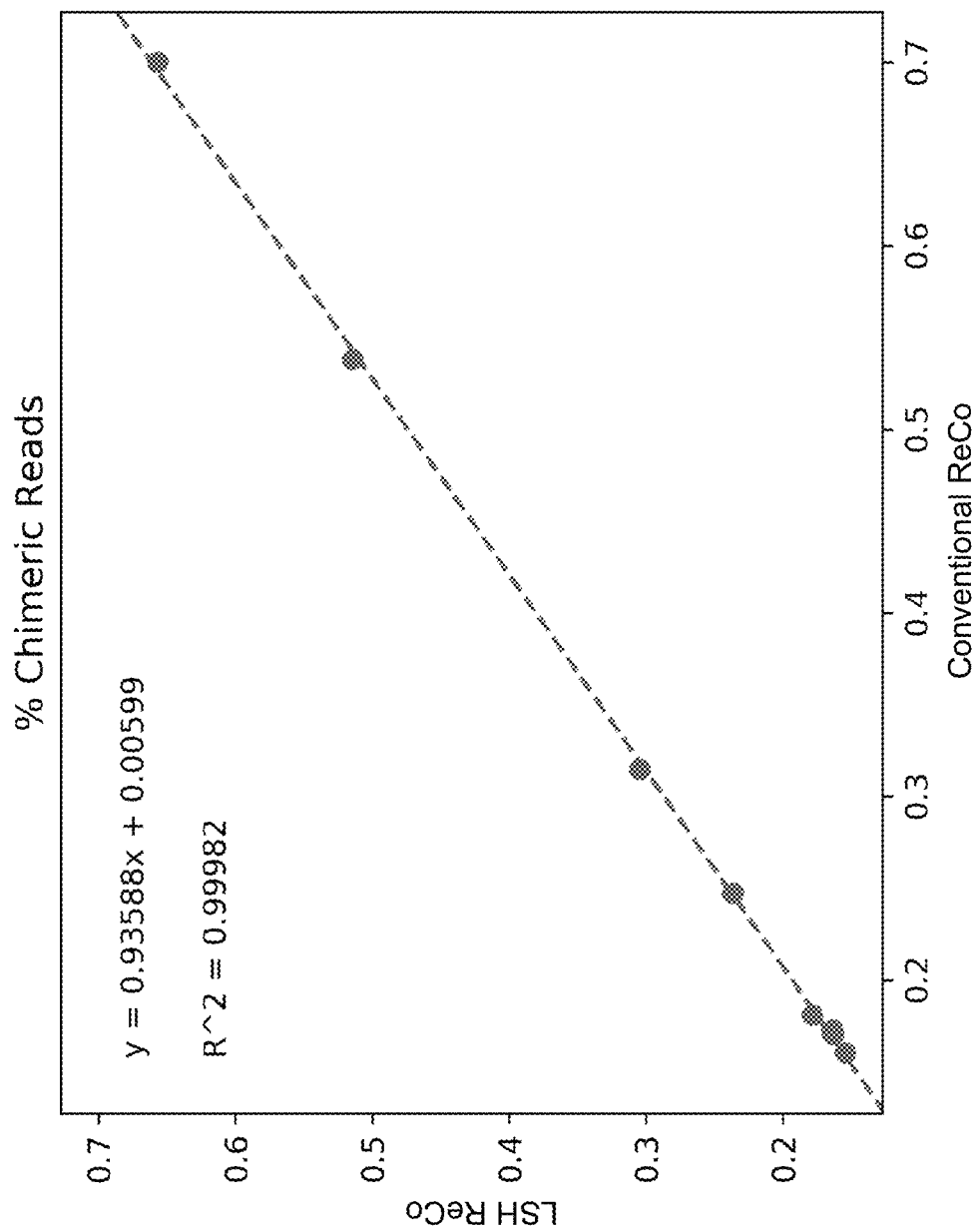
Figure 6D:
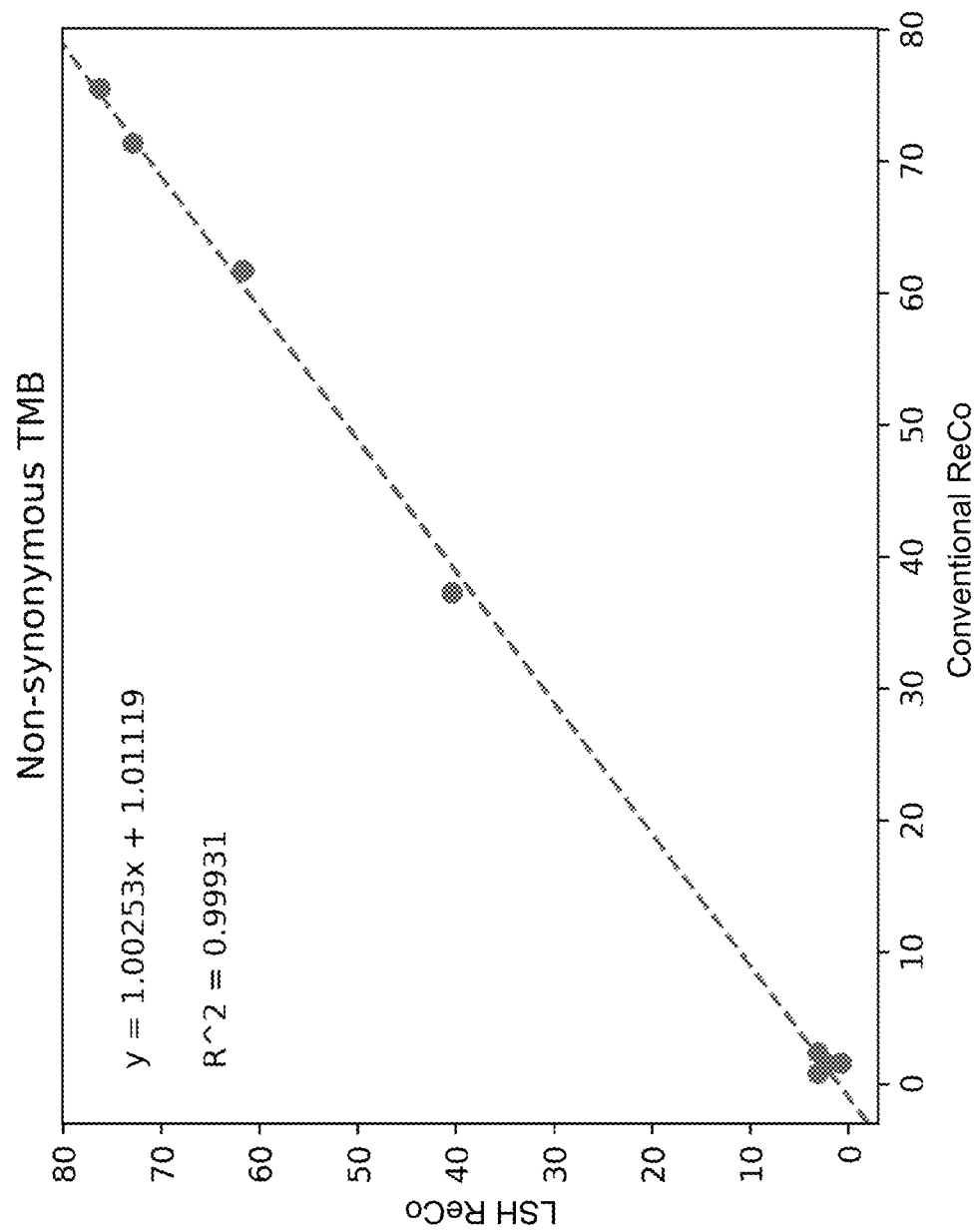
Figure 6E:
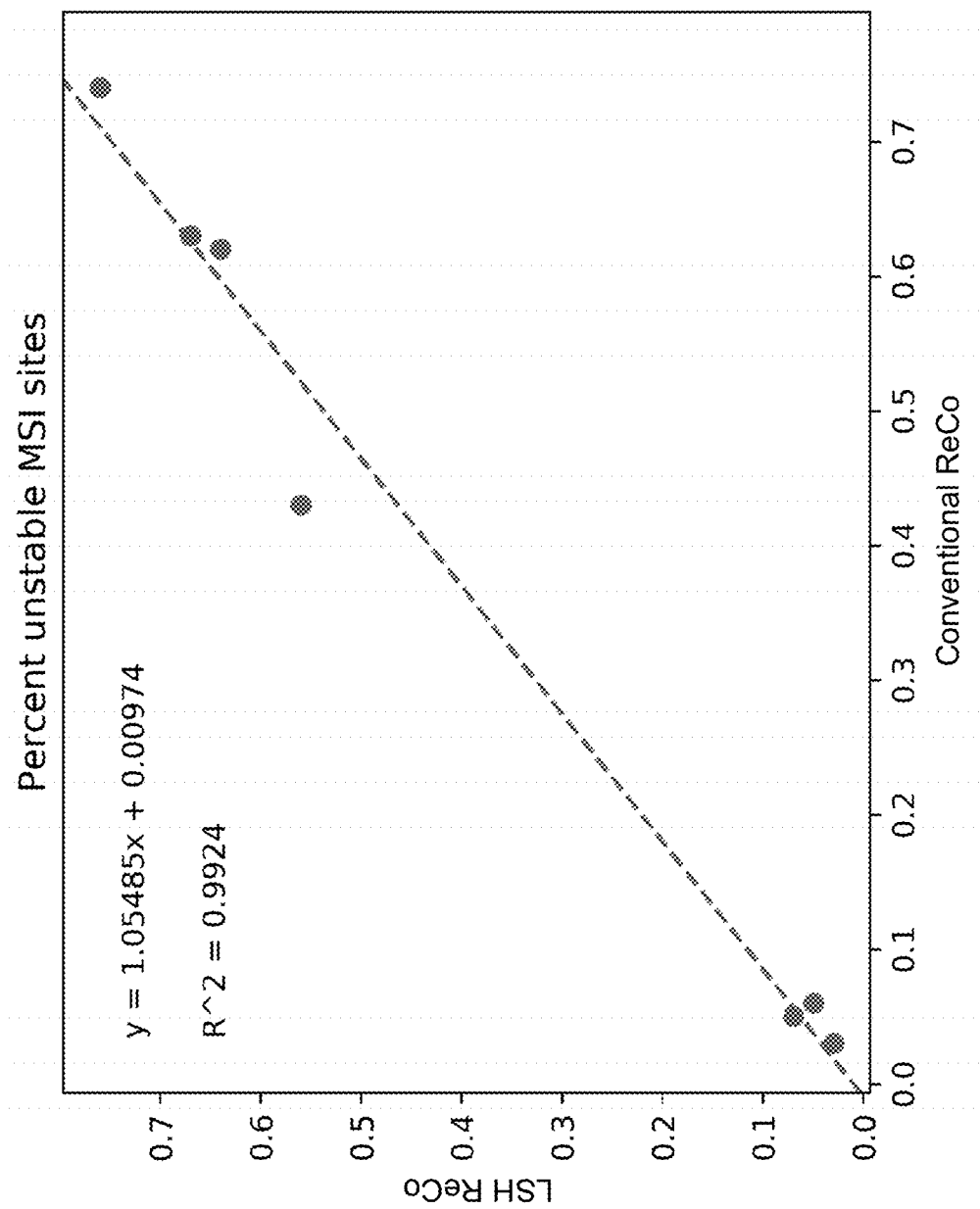
Figure 6F:
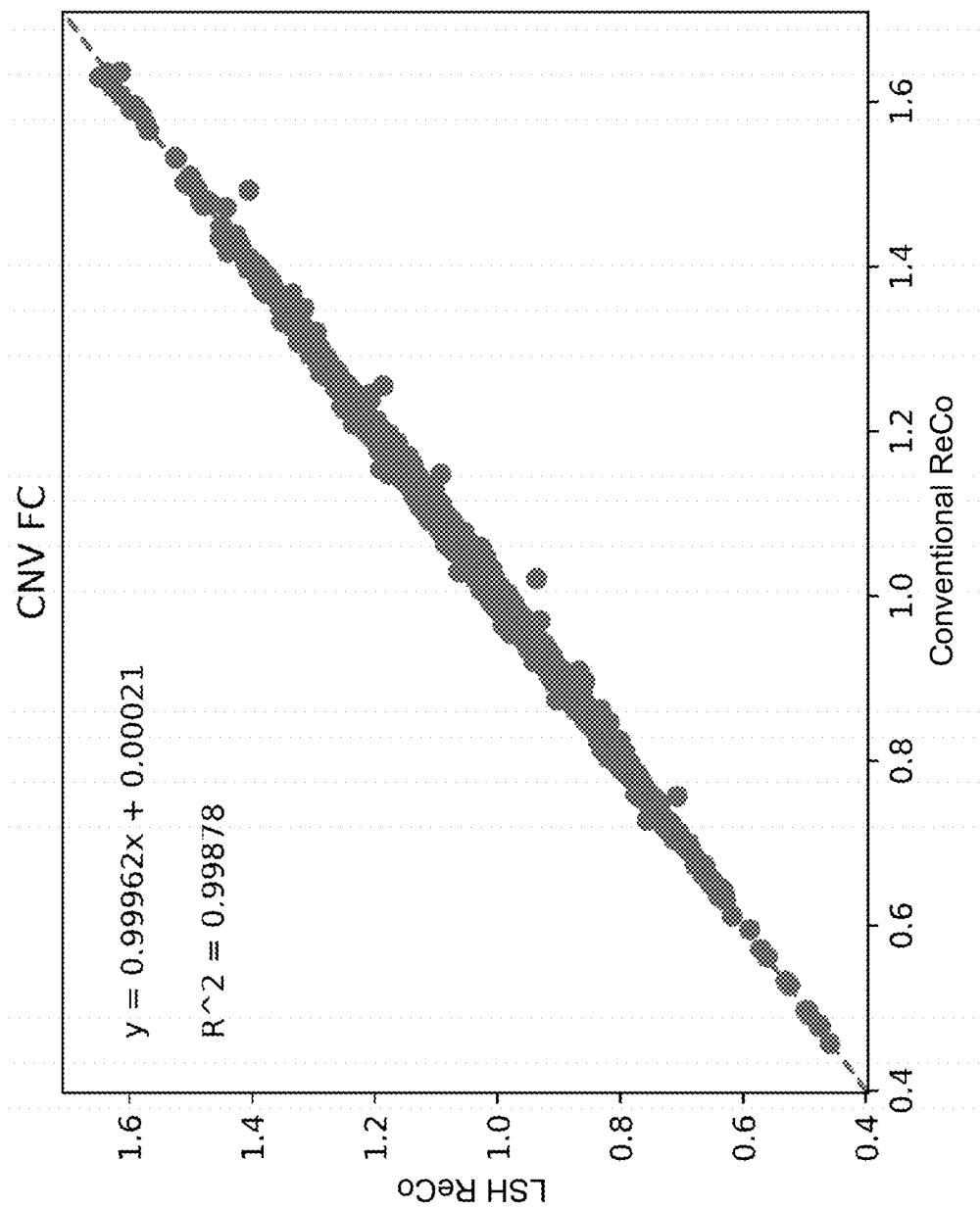

FIGS. 6A-6F are exemplary plots showing that read collapsing with locality sensitive hashing and alignment-based read collapsing have similar performance of a Next-Seq® (Illumina, Inc. (San Diego, Calif.)) run with a formalin-fixed paraffin-embedded (FFPE) sample. FIG. 6A shows extremely similar target region coverage produced by alignment based read collapsing and LSH-based read collapsing (which is also referred to herein as "fastq-based collapsing" or "fastq read collapsing"). FIG. 6B shows noise AF, which measures the proportion of genomic loci that carry non-reference evidence and is an indicator of small variant calling performance. LSH-based read collapsing had a similar error detection and correction capacity as alignment collapsing. FIG. 6C shows percentage of reads that have nonlinear alignments, which is an indicator of SV calling performance. LSH-based read collapsing produced fewer (~7%) chimeric reads. The fewer chimeric reads produced are evidence that LSH-based read collapsing is better able to generalize to noisy reads, and thus produces cleaner alignments. FIG. 6D shows tumor mutation burden (TMB), which measures mutations per megabase. The figure indicates that small variant calling was highly concordant. LSH-based read collapsing had no trouble separating reads that carry mutations from "wildtype" reads, even without guidance of a genome. FIG. 6E shows microsatellite instability, which measures mutations in highly repetitive regions of the genome. Highly repetitive regions are difficult regions to handle due to low sequence complexity/uniqueness. LSH-based read collapsing worked even in such low-complexity regions. FIG. 6F shows LSH-based read collapsing worked well even in regions with variable copy number. Table 1 shows that fusion calling exhibited dramatically improved specificity with LSH-based read collapsing as no fusion calls were expected in these samples. The fusion calling result suggests improved handling of nonlinear reads.

Table 2 shows that improvements to fusion calling specificity did not negatively impact recall of a NovaSeq™ (Illumina, Inc.) run.

TABLE 1

Fusion Calling False Positives

| Across 8 samples | Alignment-based collapser | LSH-based collapser |
|---|---|---|
| False positives after filtering | 22 | 1 |

TABLE 2

Fusion Calling Recalls.

| Fusion Gene Pair | Breakpoint 1 | Breakpoint 2 | Support Fusion (Conventional ReCo) | Support WT (Conventional ReCo) | VF (Conventional ReCo) | Support Fusion (LSH ReCo) | Support WT (LSH ReCo) | VF (LSH ReCo) |
|---|---|---|---|---|---|---|---|---|
| TMP3 \| NTRK1 | chr1: 154137492 | chr1: 156843543 | 80 | 3280 | 2.44% | 80 | 3264 | 2.45% |
| TMP3 \| NTRK1 | chr1: 154137489 | chr1: 156843542 | 80 | 3287 | 2.43% | 78 | 3279 | 2.34% |
| RET \| CCDC6 | chr10: 43609948 | chr10: 61638611 | 68 | 2966 | 2.30% | 70 | 2943 | 2.38% |
| ROS1 \| SLC34A2 | chr4: 25666629 | chr6: 117658325 | 45 | 1387 | 3.24% | 45 | 1373 | 3.28% |
| ROS1 \| SLC34A2 | chr4: 25666625 | chr6: 117658307 | 3 | 1160 | 0.26% | 3 | 1153 | 0.26% |
| ALK \| NPM1 | chr2: 29447103 | chr5: 170819618 | 10 | 2428 | 0.41% | 10 | 2400 | 0.42% |
| ALK \| NPM1 | chr2: 29447024 | chr5: 170819667 | 6 | 2650 | 0.23% | 6 | 2614 | 0.23% |
| ALK \| EML4 | chr2: 29448092 | chr2: 42493956 | 10 | 2591 | 0.39% | 11 | 2570 | 0.43% |

Altogether, these data show that LSH-based read collapsing compared favorably to alignment-based collapsing and matched or exceeded existing performance on summary-level metrics, as well as with variant calling.

Read Collapsing Method

Figure 7:
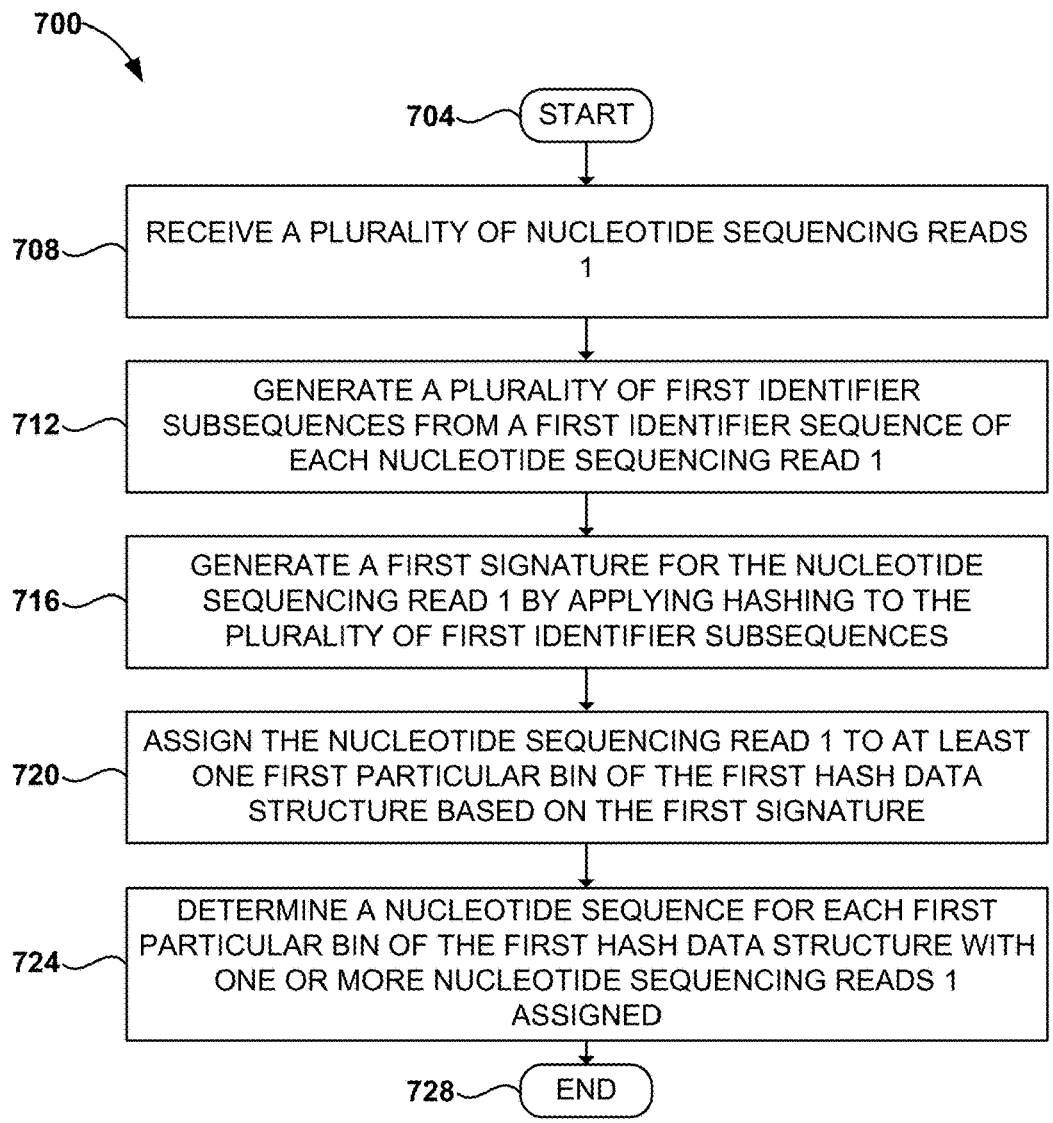
FIG. 7 is a flow diagram showing an exemplary method of read collapsing using locality sensitive hashing.

FIG. 7 is a flow diagram showing an exemplary method 700 of read collapsing using locality sensitive hashing. The method 700 may be embodied in a set of executable program instructions stored on a computer-readable medium, such as one or more disk drives, of a computing system. For example, the computing system 900 shown in FIG. 9 and described in greater detail below can execute a set of executable program instructions to implement the method 700. When the method 700 is initiated, the executable program instructions can be loaded into memory, such as RAM, and executed by one or more processors of the computing system 900. Although the method 700 is described with respect to the computing system 900 shown in FIG. 9, the description is illustrative only and is not intended to be limiting. In some embodiments, the method 700 or portions thereof may be performed serially or in parallel by multiple computing systems. The computing system 900 can include a first hash data structure, such as a hash table, for storing nucleotide sequencing reads in a plurality of bins.

After the method 700 begins at block 704, the method 700 proceeds to block 708, where a computing system receive a plurality of first nucleotide sequencing reads. The plurality of first nucleotide sequencing reads may be associated with an identical physical identifier sequence. The plurality of first nucleotide sequencing reads may not be associated any physical identifier sequence.

The method 700 proceeds from block 708 to block 712, where the computing system generating a plurality of first identifier subsequences from a first identifier sequence of each first nucleotide sequencing read. Generating the plurality of first identifier subsequences may comprise generating a plurality of k-mers from the first identifier sequence of the sequencing read. The subsequence may comprise a nucleotide insertion, a nucleotide deletion, a nucleotide substitution, or a combination thereof. Two consecutive first identifier subsequences may overlap. For example, the two consecutive first identifier subsequences overlap by k−1 nucleotides. For example, the plurality of first identifier subsequences comprises a plurality of 4-mers, and wherein the first identifier sequence comprises about 25 nucleotides. The first identifier sequence may be a subsequence of the sequencing read 1. The subsequence may be a continuous subsequence of the sequencing read 1. The subsequence may be a non-continuous subsequence of the sequencing read 1.

After generating the first identifier subsequences at block 712, the method 700 proceeds to block 716, where the computing system generates a first signature for the first nucleotide sequencing read by applying hashing to the plurality of first identifier subsequences. The first signature may match a key of the first particular bin of the first hash data structure. The first signature and the key of the first particular bin of the first hash data structure may be identical.

Generating the first signature may comprise determining a plurality of hashes for each first identifier subsequence. Generating the first signature may comprise determining each first element of the first signature from corresponding hashes of the plurality of first identifier subsequences. Each first element of the first signature may be a minimum of the corresponding hashes of the plurality of first identifier subsequences. Each first element of the first signature is a minimum, a mean, a medium, or a maximum of the corresponding hashes of the plurality of first identifier subsequences.

The method proceeds from block 716 to block 720, where the computing system assign the first nucleotide sequencing read to at least one first particular bin of the first hash data structure based on the first signature. In one embodiment, assigning the first nucleotide sequencing read comprises determining a plurality of subsequences of the first signature from the first signature of the first nucleotide sequencing read; and assigning the first nucleotide sequencing read to a first particular bin of each first hash data structure of a plurality of first hash data structures based on a subsequence of the first signature. In another embodiment, assigning the first nucleotide sequencing read comprises: determining a plurality of subsequences of the first signature from the first signature of the first nucleotide sequencing read; and assigning the first nucleotide sequencing read to a plurality of first particular bins of the first hash data structure based on the plurality of subsequences of the first signature. The method 700 ends at block 728.

In one example, the first particular bin is an existing bin of the first hash data structure, and wherein an alignment score of the first nucleotide sequencing read and a signature of another first nucleotide sequencing read assigned to the first particular bin of the first hash data structure is above an alignment score threshold. In another example, the first particular bin is an existing bin of the first hash data structure, and wherein the highest alignment score of the first nucleotide sequencing read and a signature of any first nucleotide sequencing read assigned to the first particular bin of the first hash data structure is above an alignment score threshold. In another example, the first particular bin is a new bin of the first hash data structure, and wherein an alignment score of the first nucleotide sequencing read and a signature of any first nucleotide sequencing read assigned to any existing bin of the first hash data structure is below an alignment score threshold.

After the first nucleotide sequencing read is assigned to the first particular bin at block 720, the method 700 proceeds to block 724, where the computing system determines a nucleotide sequence for each first particular bin of the first hash data structure with one or more first nucleotide sequencing reads assigned. Determining the nucleotide sequence may comprise determining a consensus sequence of the one or more first nucleotide sequencing reads assigned to the first particular bin. Determining the consensus sequence may comprise determining a most frequent first nucleotide sequencing read assigned to the first particular bin as the consensus sequence of the first particular bin. The consensus sequence may comprise a most frequent nucleotide base for each corresponding position of the first nucleotide sequencing reads assigned to the first particular bin. Determining the consensus sequence may comprise determining a first nucleotide sequencing read with a highest quality score assigned to the first particular bin as the consensus sequence of the first particular bin. The highest quality score may be determined based on a quality score of each base on the first nucleotide sequencing read with the highest quality score. Determining the nucleotide sequence may comprise selecting a sequence of the one or more first nucleotide sequencing reads assigned to the first particular bin as a representative sequence of the first particular bin. Determining the nucleotide sequence may comprise determining an alignment score of two of the one or more first nucleotide sequencing reads assigned to the first particular bin is above an alignment score threshold.

Paired-End Sequencing Reads.

Each first nucleotide sequencing read may be associated with a second nucleotide sequencing read. The first nucleotide sequencing read and the second nucleotide sequencing read may form paired-end nucleotide sequencing reads. The computing system may generate a plurality of second identifier subsequences from a second identifier sequence of the second nucleotide sequencing read; and generate a second signature of the second nucleotide sequencing read by applying hashing to the plurality of second identifier subsequences.

Assigning the first nucleotide sequencing read may be different in different implementations. For example, assigning the first nucleotide sequencing read comprises assigning a pair of sequencing reads comprising the first nucleotide sequencing read and the second nucleotide sequencing read to the first particular bin of the first hash data structure based on the first signature. As another example, assigning the first nucleotide sequencing read comprises assigning the second nucleotide sequencing read to a second particular bin of the first hash data structure based on the second signature. As yet another example, assigning the first nucleotide sequencing read comprises assigning a pair of sequencing reads comprising the first nucleotide sequencing read and the second nucleotide sequencing read to a second particular bin of a second hash data structure based on the second signature.

As an example, assigning the first nucleotide sequencing read comprises assigning a pair of sequencing reads comprising the first nucleotide sequencing read and the nucleotide sequencing read to the first particular bin of the first hash data structure and a second particular bin of a second data structure based on the plurality of subsequences of the first signature of the first nucleotide sequencing read and a plurality of subsequences of the second signature of the second nucleotide sequencing read, respectively. The computing system may store a first data structure and a second data structure for storing keys of bins of the first hash data structure and keys of bins of the second hash data structure, respectively. Assigning the pair of sequencing reads may comprise determining the first signature and the second signature are stored in the first data structure and the second data structure; and assigning the pair of sequencing reads to the first particular bin of the first hash data structure and the second particular bin of the second hash data structure using the first stored key and the second stored key, respectively. An alignment score of the pair of sequencing reads and a pair comprising a first sequencing read associated with the first stored key and a second sequencing read associated with the second stored key is above an alignment score threshold.

Assigning the pair of sequencing reads may comprise determining one or more first keys of the first hash data structure stored in the first data structure and associated with the first signature; determining one or more second keys of the second hash data structure stored in the second data structure and associated with the second signature; determining a pair comprising a first sequencing read associated with a first stored key and a second sequencing read associated with a second stored key has a highest alignment score of any pair comprising a first sequencing read associated with any first stored key and a second sequencing read associated with any second stored key with the pair of sequencing reads; and assigning the pair of sequencing reads to the first particular bin of the first hash data structure and the second particular bin of the second hash data structure using the first stored key and the second stored key associated with the pair of first sequencing read and second sequencing read with the highest alignment score, respectively. The first sequencing read associated with the first stored key may have a highest alignment score of the first sequencing read associated with any first stored key with the first signature. The second sequencing read associated with the second stored key may have a highest alignment score of the second sequencing read associated with any second stored key with the second signature.

Read Identification

Figure 8:
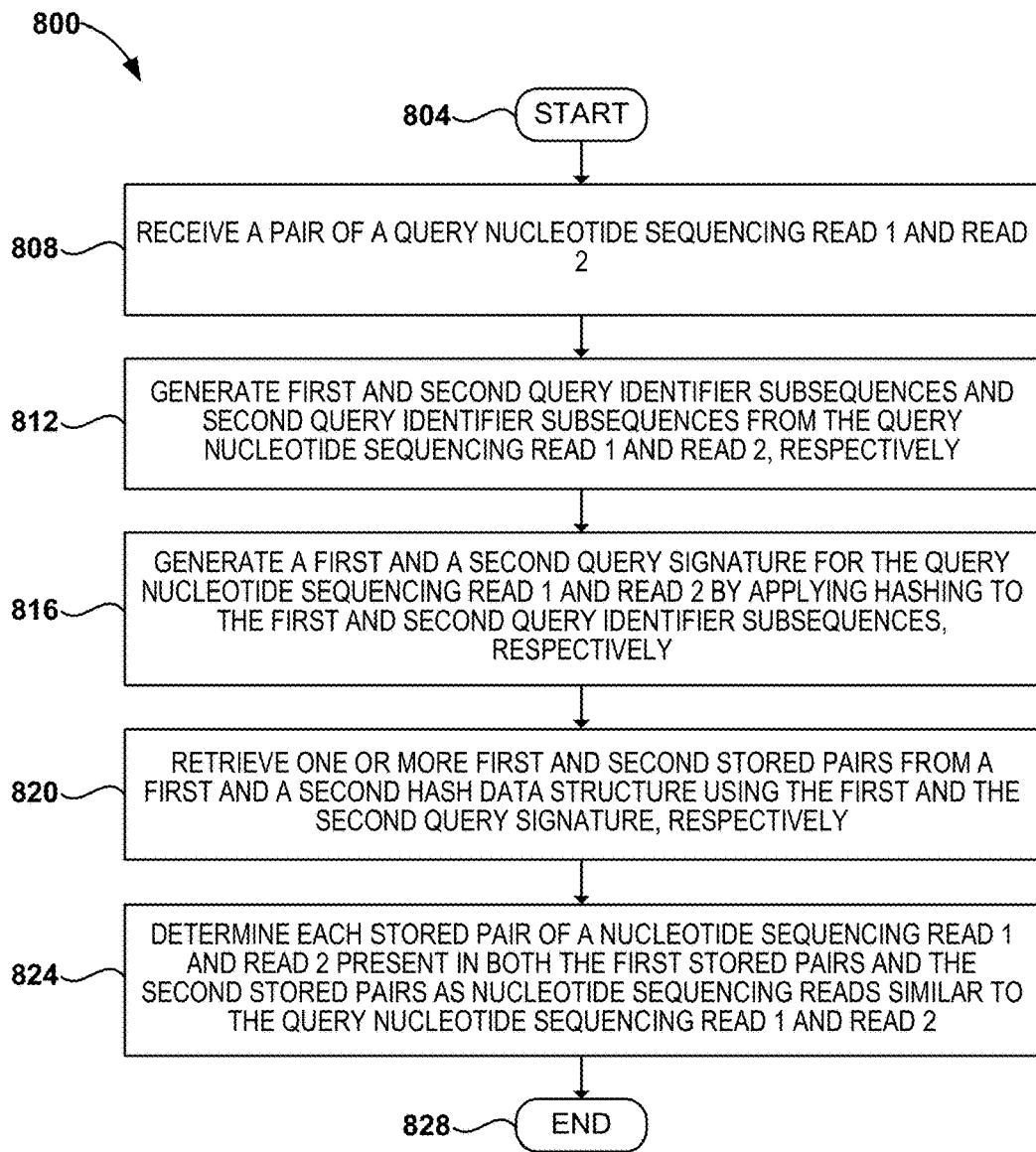
FIG. 8 is a flow diagram showing an exemplary method of identifying similar reads using locality sensitive hashing.

FIG. 8 is a flow diagram showing an exemplary method 800 of identifying similar reads using locality sensitive hashing. The method 800 may be embodied in a set of executable program instructions stored on a computer-readable medium, such as one or more disk drives, of a computing system. For example, the computing system 900 shown in FIG. 9 and described in greater detail below can execute a set of executable program instructions to implement the method 800. When the method 800 is initiated, the executable program instructions can be loaded into memory, such as RAM, and executed by one or more processors of the computing system 900. Although the method 800 is described with respect to the computing system 900 shown in FIG. 9, the description is illustrative only and is not intended to be limiting. In some embodiments, the method 800 or portions thereof may be performed serially or in parallel by multiple computing systems. The computing system may store a first hash data structure and a second hash data structure for storing a plurality of pairs of sequencing reads.

Each pair of sequencing reads may comprise a first nucleotide sequencing read and a second nucleotide sequencing read, wherein each pair of sequencing reads is assigned to one of a plurality of first bins of the first hash data structure based on a first signature of a first nucleotide sequencing read of the pair generated by hashing first identifier subsequences of a first identifier sequence of the first nucleotide sequencing read. Each pair of sequencing reads may be assigned to one of a plurality of second bins of the second hash data structure based on a second signature of a second nucleotide sequencing read of the pair generated by hashing second identifier sequences of the second nucleotide sequencing read.

After the method 800 begins at block 804, the method 800 proceeds to block 808, where a computing system receives a pair of a first query nucleotide sequencing read and a second query nucleotide sequencing read. The method 800 proceeds from block 808 to block 812, where the computing system generates a plurality of first query identifier subsequences and a plurality of second query identifier subsequences from the first query nucleotide sequencing read and the second query nucleotide sequencing read, respectively. After generating the query identifier subsequences at block 812, the method 800 proceeds to block 816, where the computing system generates a first query signature and a second query signature for the first nucleotide sequencing read and the second nucleotide sequencing read by applying hashing to the plurality of first query identifier subsequences and the plurality of second query identifier subsequences, respectively. The computing system may perform the steps at blocks 808-816 as described with reference to blocks 708-716 described with reference to FIG. 7.

After block 816, the method may include orthogonal querying. For example, the method proceeds from block 816 to block 820, where the computing system retrieves one or more first stored pairs and one or more second stored pairs from the first hash data structure and the second hash data structure using the first query signature and the second query signature, respectively, where each of the first pairs and the second pairs comprises a first stored nucleotide sequencing read and a second stored nucleotide sequencing read. After retrieving pairs of sequencing reads at block 820, the method 800 proceeds to block 824, where the computing system determines each pair of a first stored nucleotide sequencing read and a second stored nucleotide sequencing read present in both the first stored pairs and second stored pairs as a sequencing read 1 and sequencing read 2 as being similar to the query sequencing read 1 and the query sequencing read 2. The method 800 ends at block 828.

Each pair of sequencing reads may be associated with a first identifier sequence and a second identifier sequence. The computing system may determine the first identifier sequence and the second identifier sequence of a first pair of sequencing reads and the second identifier sequence and the first identifier sequence of a second pair of sequencing reads are identical; and determine a nucleotide sequence of the first pair of sequencing reads and the second pair of sequencing reads.

In one embodiment, the method 800 may include receiving a first query nucleotide sequencing read at block 808. Receiving the first query nucleotide sequencing read may include receiving a pair of the first query nucleotide sequencing read and a second query nucleotide sequencing read. The method 800 may include generating a plurality of first query identifier subsequences from the first query nucleotide sequencing read at block 812. Generating the plurality of first query identifier subsequences may include generating a plurality of second query identifier subsequences from the second nucleotide sequencing read. The method 800 may include generating a first query signature for the first nucleotide sequencing read by applying hashing to the plurality of first query identifier subsequences at block 816. Generating the first query signature may include generating a second query signature for the second nucleotide sequencing read by applying hashing to the plurality of second query identifier subsequences. The method 800 may include retrieving one or more first stored nucleotide sequencing reads from a first hash data structure using the first query signature at block 820. Each of the first stored nucleotide sequencing reads may be similar to the first query nucleotide sequencing read. Retrieving one or more first stored nucleotide sequencing reads may include retrieving one or more first stored pairs from the first hash data structure, storing a plurality of pairs of sequencing reads, using the first query signature and the second query signature. Each of the first pairs may include a first stored nucleotide sequencing read and a second stored nucleotide sequencing read similar to the first query nucleotide sequencing read and the second query nucleotide sequencing read, respectively.

Execution Environment

Figure 9:
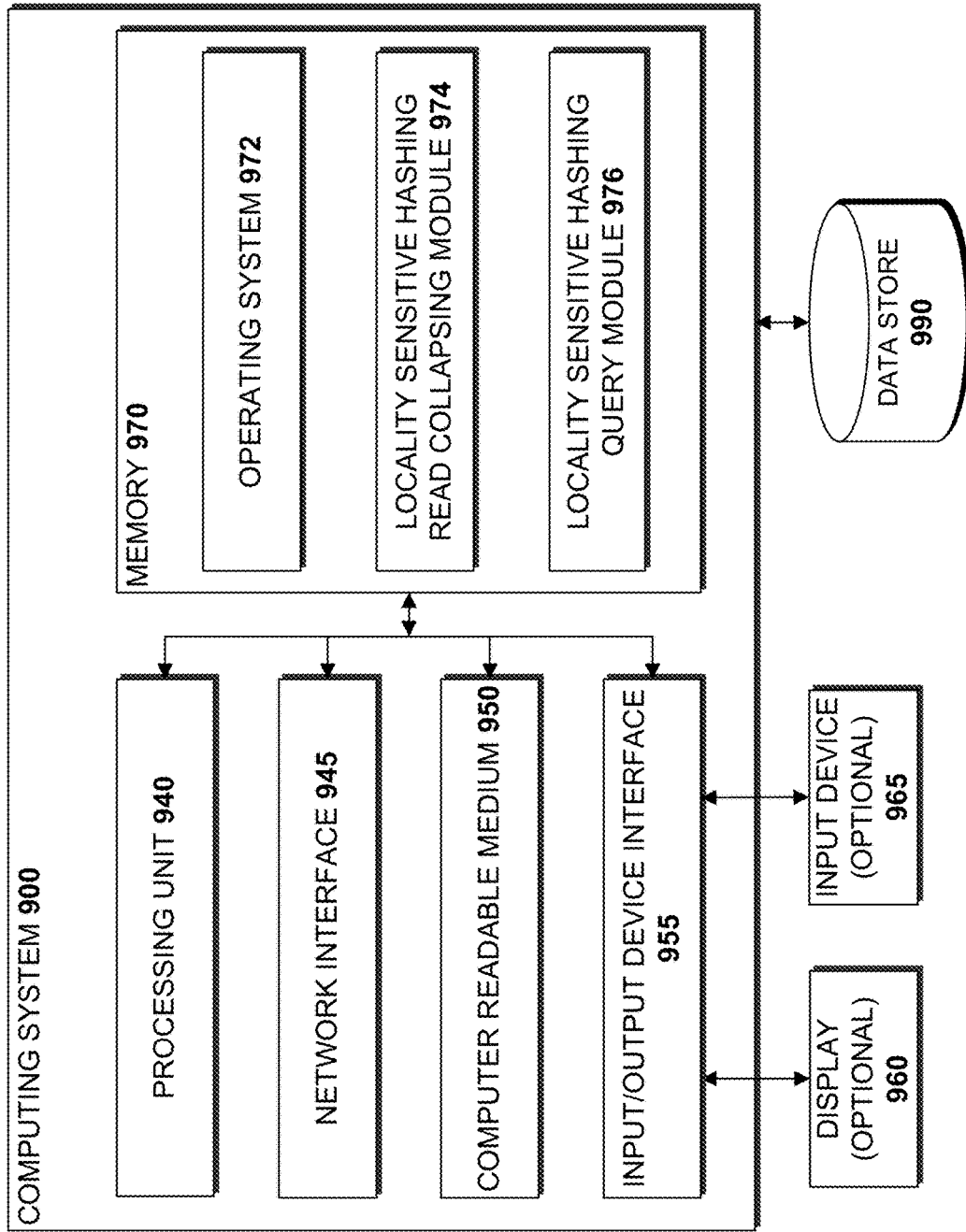
FIG. 9 is a block diagram of an illustrative computing system configured to implement read collapsing and querying with locality sensitive hashing.

FIG. 9 depicts a general architecture of an example computing device 900 configured to implement the metabolite, annotation and gene integration system disclosed herein. The general architecture of the computing device 900 depicted in FIG. 9 includes an arrangement of computer hardware and software components. The computing device 900 may include many more (or fewer) elements than those shown in FIG. 9. It is not necessary, however, that all of these generally conventional elements be shown in order to provide an enabling disclosure. As illustrated, the computing device 900 includes a processing unit 940, a network interface 945, a computer readable medium drive 950, an input/output device interface 955, a display 960, and an input device 965, all of which may communicate with one another by way of a communication bus. The network interface 945 may provide connectivity to one or more networks or computing systems. The processing unit 940 may thus receive information and instructions from other computing systems or services via a network. The processing unit 940 may also communicate to and from memory 970 and further provide output information for an optional display 960 via the input/output device interface 955. The input/output device interface 955 may also accept input from the optional input device 965, such as a keyboard, mouse, digital pen, microphone, touch screen, gesture recognition system, voice recognition system, gamepad, accelerometer, gyroscope, or other input device.

The memory 970 may contain computer program instructions (grouped as modules or components in some embodiments) that the processing unit 940 executes in order to implement one or more embodiments. The memory 970 generally includes RAM, ROM and/or other persistent, auxiliary or non-transitory computer-readable media. The memory 970 may store an operating system 972 that provides computer program instructions for use by the processing unit 940 in the general administration and operation of the computing device 900. The memory 970 may further include computer program instructions and other information for implementing aspects of the present disclosure.

For example, in one embodiment, the memory 970 includes a locality sensitive hashing-based read collapsing module 974 for collapsing sequencing reads using locality sensitive hashing, such as the reads collapsing method 700 described with reference to FIG. 7. The memory 970 may additionally or alternatively include a locality sensitive hashing query module 976 for identifying similar nucleotide sequencing reads of a query sequencing read, such as the identification method 800 described with reference to FIG. 8. In addition, memory 970 may include or communicate with the data store 990 and/or one or more other data stores that store data for and results of reads collapsing and/or similar nucleotide sequencing reads identification.

Hardware Acceleration

In some embodiments, the disclosed methods for grouping and collapsing sequencing reads are implemented in an application-specific hardware designed or programmed to compute the disclosed methods with higher efficiency than a general-purpose computer processor. For example, the processing unit 940 may be a field-programmable gate array (FPGA) or an application-specific integrated circuit (ASIC).

In one example, the locality sensitive hashing (LSH) operation may be accelerated by a FPGA. In some embodiments, acceleration of the LSH operation by FPGA may depend on the memory required to build and query the hash tables per UMI, and also on how close memory bandwidth is to being a bottleneck in software. If clustering UMIs associated with sequencing reads is implemented in a FPGA, then it may be beneficial to also accelerate the read collapsing methods within the same hardware.

In some embodiments, one or more Application-Specific Integrated Circuits (ASICs) can be programmed to perform the functions of one or more of the respective genomic analysis modules, or other computers, described herein. ASICs include integrated circuits that include one or more programmable logic circuits that are similar to the FPGAs described herein in that the digital logic gates of the ASIC are programmable using a hardware description language such VHDL. However, ASICs differ from FPGAs in that ASICs are programmable only once and cannot be dynamically reconfigured once programmed. Furthermore, aspects of the present disclosure are not limited to implementing grouping and collapsing sequencing reads, using FPGAs or ASICs. Instead, any of the genomic analysis modules, or other computers, of the processing unit 940 can be implemented using one or more central processing units (CPUs), graphical processing units (GPUs), or any combination therefore that implement grouping and collapsing sequencing reads through the execution of software instructions.

In some implementations, the use of integrated circuits such as an FPGA, ASIC, CPU, GPU, or combination thereof, to implement grouping and collapsing sequencing reads can include a single FPGA, a single ASIC, a single CPU, a single GPU, or any combination thereof. Alternatively, or in addition, the use of integrated circuits such as FPGA, ASIC, CPU, GPU, or combination thereof, to implement grouping and collapsing sequencing reads can include multiple FPGAs, multiple ASICs, multiple CPUs, or multiple GPUs, or any combination thereof. The use of additional integrated circuits such as multiple FPGAs to implement grouping and collapsing sequencing reads can reduce the amount of time it takes to perform secondary analysis operations such as mapping, aligning, P-HMM probability calculations, and variant calling. In some implementations, use of the FPGA to implement these secondary analysis operations can reduce the time it takes to complete these secondary analysis operations from 24 hours, or more, to as little as 30 minutes, or less. In some implementations, the use of the multiple FPGAs to perform these secondary analysis operations can result in the completion of these secondary analysis operations in as little as 5 minutes.

Terminology

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for determining a nucleotide sequence from nucleotide sequencing reads, comprising:
    a non-transitory memory configured to store executable instructions and a first hash data structure for storing nucleotide sequencing reads in a plurality of bins; and
    a hardware processor programmed by the executable instructions to perform:
        receiving a plurality of first nucleotide sequencing reads;
        for each first nucleotide sequencing read:
            generating a plurality of first identifier subsequences from a first identifier sequence of the first nucleotide sequencing read that are consecutive subsequences of the first identifier sequence;
            for each first identifier subsequence, determining a plurality of hashes using a plurality of hash functions;
            generating a first signature for the first nucleotide sequencing read comprising a plurality of first signature hashes each for a different first position, wherein each first signature hash is the minimum of the hashes determined for the plurality of first identifier subsequences at the first position; and
            assigning the first nucleotide sequencing read to at least one first particular bin of the first hash data structure based on the first signature; and
        determining a nucleotide sequence for each first particular bin of the first hash data structure with one or more first nucleotide sequencing reads assigned.

2. The system of claim 1, wherein assigning the first nucleotide sequencing read comprises:
    determining a plurality of subsequences of the first signature from the first signature of the first nucleotide sequencing read; and
    assigning the first nucleotide sequencing read to a first particular bin of each first hash data structure of a plurality of first hash data structures based on a subsequence of the first signature.

3. The system of claim 1, wherein assigning the first nucleotide sequencing read comprises:
    determining a plurality of subsequences of the first signature from the first signature of the first nucleotide sequencing read; and
    assigning the first nucleotide sequencing read to a plurality of first particular bins of the first hash data structure based on the plurality of subsequences of the first signature.

4. The system of claim 1, wherein the first particular bin is an existing bin of the first hash data structure, and wherein an alignment score of the first nucleotide sequencing read and another first nucleotide sequencing read assigned to the first particular bin of the first hash data structure is above an alignment score threshold.

5. The system of claim 1, wherein the first particular bin is an existing bin of the first hash data structure, and wherein the highest alignment score of the first nucleotide sequencing read and any first nucleotide sequencing read assigned to the first particular bin of the first hash data structure is above an alignment score threshold.

6. The system of claim 1, wherein the first particular bin is a new bin of the first hash data structure, and wherein an alignment score of the first nucleotide sequencing read and any first nucleotide sequencing read assigned to any existing bin of the first hash data structure is below an alignment score threshold.

7. The system of claim 1, wherein the first signature matches a key of the first particular bin of the first hash data structure.

8. The system of claim 1, wherein the first signature and the key of the first particular bin of the first hash data structure are identical.

9. The system of claim 1, wherein each first nucleotide sequencing read is associated with a second nucleotide sequencing read, and wherein the first nucleotide sequencing read and the second nucleotide sequencing read form are paired-end nucleotide sequencing reads.

10. The system of claim 1, wherein determining the nucleotide sequence comprises determining a consensus sequence of the one or more first nucleotide sequencing reads assigned to the first particular bin.

11. The system of claim 10, wherein determining the consensus sequence comprises determining a first nucleotide sequencing read with a highest quality score assigned to the first particular bin as the consensus sequence of the first particular bin.

12. The system of claim 1, wherein determining the nucleotide sequence comprises selecting a sequence of the one or more first nucleotide sequencing reads assigned to the first particular bin as a representative sequence of the first particular bin.

13. The system of claim 1, wherein determining the nucleotide sequence comprises determining an alignment score of two of the one or more first nucleotide sequencing reads assigned to the first particular bin is above an alignment score threshold.

14. The system of claim 1, wherein the plurality of nucleotide sequencing reads is associated with an identical physical identifier sequence.

15. The system of claim 1, wherein the plurality of nucleotide sequencing reads is not associated any physical identifier sequence.

16. The system of claim 9, wherein assigning the first nucleotide sequencing read comprises assigning a pair of sequencing reads comprising the first nucleotide sequencing read and the second nucleotide sequencing read to the first particular bin of the first hash data structure based on the first signature.

17. A computer-implemented method for determining a nucleotide sequence from nucleotide sequencing reads, comprising:
   receiving a plurality of first nucleotide sequencing reads;
   for each first nucleotide sequencing read:
      generating a plurality of first identifier subsequences from a first identifier sequence of the first nucleotide sequencing read;
      for each first identifier subsequence, determining a plurality of hashes using a plurality of hash functions;
      generating a first signature for the first nucleotide sequencing read comprising a plurality of first signature hashes each for a different first position, wherein each first signature hash is selected from the hashes determined for the plurality of first identifier subsequences at the first position of the first signature hash; and
      assigning the first nucleotide sequencing read to a first particular bin of a first data structure based on the first signature; and
   determining a nucleotide sequence for each first particular bin of the first data structure with one or more first nucleotide sequencing reads assigned.

18. The method of claim 17, wherein generating the plurality of first identifier subsequences comprises generating a plurality of k-mers from the first identifier sequence of the sequencing read.

19. The method of claim 17, wherein the subsequence comprises a nucleotide insertion, a nucleotide deletion, a nucleotide substitution, or a combination thereof.

20. The method of claim 17, wherein two consecutive first identifier subsequences overlap.

21. The method of claim 18, wherein the plurality of first identifier subsequences comprises a plurality of 4-mers, and wherein the first identifier sequence comprises about 25 nucleotides.

22. The method of claim 18, wherein the first identifier sequence is a subsequence of the first nucleotide sequencing read.

23. The method of claim 17, wherein the first data structure comprises a hash table.

24. A system for identifying similar nucleotide sequencing reads, comprising:
   non-transitory memory configured to store: executable instructions, a first hash data structure and a second hash data structure for storing a plurality of pairs of sequencing reads; and
   a hardware processor programmed by the executable instructions to perform:
      receiving a pair of a first query nucleotide sequencing read and a second query nucleotide sequencing read, wherein the first query nucleotide sequencing read and the second query nucleotide sequencing read are paired-end nucleotide sequencing reads;
      generating (i) a plurality of first query identifier subsequences from the first query nucleotide sequencing read, and (ii) a plurality of second query identifier subsequences from the second query nucleotide sequencing read;
      determining (i) for each first query identifier subsequence, a plurality of first query hashes, and (ii) for each second query identifier subsequence, a plurality of second query hashes, using a plurality of hash functions;
      generating a first query signature for the first query nucleotide sequencing read comprising a plurality of first query signature hashes each for a different first position, and (ii) a second query signature for the second query nucleotide sequencing read comprising a plurality of second query signature hashes each for a different second position, wherein each first query signature hash is selected from the first hashes determined for the plurality of first query identifier subsequences at the first position of the first query signature hash, and wherein each second query signature hash is selected from the second hashes determined for the plurality of second query identifier subsequences at the second position of the second query signature hash;
      retrieving (i) one or more first stored pairs from the first hash data structure using the first query signature, and (ii) one or more second stored pairs from the second hash data structure using the second query signature, wherein each first stored pair comprises a first stored nucleotide sequencing read and a second stored nucleotide sequencing read that are paired-end nucleotide sequencing reads, and wherein each second stored pair comprises a first stored nucleotide sequencing read and a second stored nucleotide sequencing read that are paired-end nucleotide sequencing reads; and
      determining, for each pair of a first stored nucleotide sequencing read and a second stored nucleotide sequencing read present in both the first stored pairs and second stored pairs, the first stored nucleotide sequencing read and the second stored nucleotide sequencing read of the pair as being similar to the first query sequencing read and the second query sequencing read, respectively.

25. The system of claim 24, wherein each pair of stored sequencing reads comprises a first stored nucleotide sequencing read and a second stored nucleotide sequencing read, wherein each pair of stored sequencing reads is assigned to one of a plurality of first bins of the first hash data structure based on a first signature of a first stored nucleotide sequencing read of the pair generated by hashing first identifier subsequences of a first identifier sequence of the first stored nucleotide sequencing read, and wherein each pair of stored sequencing reads is assigned to one of a plurality of second bins of the second hash data structure based on a second signature of a second stored nucleotide sequencing read of the pair generated by hashing second identifier subsequences of a second identifier sequence of the second nucleotide sequencing read.

26. The system of claim 24, wherein the hardware processor is programmed by the executable instructions to perform:
   for each pair of sequencing reads:
      generating a plurality of first identifier subsequences from a first identifier sequence of the first nucleotide sequencing read of the pair of sequencing reads;

generating a first signature for the first nucleotide sequencing read by applying the plurality of hashing functions to the plurality of first identifier subsequences; and assigning the pair of sequencing reads to at least one first particular bin of the first hash data structure based on the first signature; and determining a first nucleotide sequence and a second nucleotide sequence for each first particular bin of the first hash data structure with one of more pairs assigned to the particular bin of the first hash data structure.

27. The system of claim 24, wherein each pair of sequencing reads is associated with a first identifier sequence and a second identifier sequence, and wherein the hardware processor is programmed by the executable instructions to perform:

determining the first identifier sequence and the second identifier sequence of a first pair of sequencing reads and the second identifier sequence and the first identifier sequence of a second pair of sequencing reads are identical, respectively; and determining a first nucleotide sequence and a second nucleotide sequence for the first pair of sequencing reads and the second pair of sequencing reads.

28. A method for identifying similar nucleotide sequencing reads, comprising:

receiving a first query nucleotide sequencing read;

generating a plurality of first query identifier subsequences from the first query nucleotide sequencing read;

for each first query identifier subsequence, determining a plurality of first query hashes using a plurality of hash functions;

generating a first query signature for the first nucleotide sequencing read comprising a plurality of first query signature hashes each for a different first position, wherein each first query signature hash is selected from the first hashes determined for the plurality of first query identifier subsequences at the first position of the first query signature hash; and retrieving one or more first stored nucleotide sequencing reads from a first hash data structure using the first query signature, wherein each of the first stored nucleotide sequencing reads is similar to the first query nucleotide sequencing read.

29. The method of claim 28, wherein receiving the first query nucleotide sequencing read comprises receiving a pair of the first query nucleotide sequencing read and a second query nucleotide sequencing read, wherein generating the plurality of first query identifier subsequences comprises generating a plurality of second query identifier subsequences from the second nucleotide sequencing read, wherein for each first query identifier subsequence, determining a plurality of first query hashes using a plurality of hash functions comprises for each second query identifier subsequence, determining a plurality of second query hashes using the plurality of hash functions, wherein generating the first query signature comprises generating a second query signature for the second nucleotide sequencing read comprising a plurality of second query signature hashes each for a different second position, wherein each second query signature hash is selected from the second hashes determined for the plurality of second query identifier subsequences at the second position of the second query signature hash, and wherein retrieving one or more first stored nucleotide sequencing reads comprises retrieving one or more first stored pairs from the first hash data structure, wherein each of the first stored pairs comprises a first stored nucleotide sequencing read and a second stored nucleotide sequencing read similar to the first query nucleotide sequencing read and the second query nucleotide sequencing read, respectively.

* * * * *

UNITED STATES PATENT AND TRADEMARK OFFICE
CERTIFICATE OF CORRECTION

PATENT NO. : 11,688,489 B2
APPLICATION NO. : 16/667642
DATED : June 27, 2023
INVENTOR(S) : Chen Zhao et al.

It is certified that error appears in the above-identified patent and that said Letters Patent is hereby corrected as shown below:

In the Claims

Column 22, Line 47 In Claim 9, change "read form" to --read--.

Column 23, Line 46 In Claim 21, change "claim 18" to --claim 17--.

Signed and Sealed this
Seventh Day of November, 2023

*Katherine Kelly Vidal*
Katherine Kelly Vidal
*Director of the United States Patent and Trademark Office*